US005707846A

United States Patent [19]

Taniguchi et al.

[11] Patent Number: 5,707,846
[45] Date of Patent: Jan. 13, 1998

[54] N-ACETYLGLUCOSAMINYL TRANSFERASE GENE CODING THEREFOR AND PROCESS FOR PRODUCTION THEREOF

[75] Inventors: Naoyuki Taniguchi; Atsushi Nishikawa, both of Toyonaka; Nozomi Yamaguchi, Kyoto, all of Japan

[73] Assignees: Suntory Limited; Naoyuki Taniguchi, both of Osaka, Japan

[21] Appl. No.: 405,230

[22] Filed: Mar. 16, 1995

Related U.S. Application Data

[62] Division of Ser. No. 110,736, Aug. 23, 1993.

[30] Foreign Application Priority Data

Aug. 24, 1992 [JP] Japan ................... 4-245950
Aug. 6, 1993 [JP] Japan ................... 5-237118

[51] Int. Cl.$^6$ .............................................. C12N 9/10
[52] U.S. Cl. ............................................... 435/193
[58] Field of Search ................................... 435/193

[56] References Cited

FOREIGN PATENT DOCUMENTS

| 91/12340 | 8/1991 | WIPO . |
| 92/09694 | 6/1992 | WIPO . |
| 94/00475 | 1/1994 | WIPO . |

OTHER PUBLICATIONS

"Isolation, Characterization, and Expression of a cDNA Encoding N–Acetyglucosaminyltransferase V", Mohamed Shoreibah et al., Departments of Biochemistry and Complex Carbohydrate Research Center, University of Georgia, Athens, Georgia, The Journal of Biological Chemistry, pp. 15381–15385, vol. 268, No. 21, Jul. 25, 1993, Baltimore, Maryland.

"Purification and Characterization of Rat Kidney UDP–N–acetylglucosamine: α–6–D–Mannoside β–1, 6–N–Acetylglucosaminyltransferase", Mohamed G. Shoreibach et al., Department of Biochemistry and Complex Carbohydrate Research Center, University of Georgia, Athens, Georgia, The Journal of Biological Chemistry, pp. 2920–2927, vol. 267, No. 5, Feb. 15, 1992, Baltimore, Maryland.

"Isolation of Putative cDNAs which Encode N–Acetyglucosaminyltransferse V. Activity", N. Fregien et al., Department of Cell Biology, University of Miami Medical School, Miami, Florida, The FASEB Journal, p. A1979, Abstract No. 1664, vol. 4, No. 5, Mar. 1990, Bethesda, Maryland.

I. Brockhausen et al., "Control of glycoprotein synthesis. The use of oligosaccharide substrates and HPLC to study the sequential pathway for n–acetylglucosaminyltransferases I, II, III, IV, V, and VI in the biosynthesis of highly branched N–glycans by hen oviduct membranes", Biochem. Cell. Biol., vol. 66, pp. 1134–1151, 1988.

M. Pierce et al., "Activity of UDP–GLCNAC:α–Mannoside β(1,6)N–Acetylglucosaminyltransferase (GnT V) in Cultured Cells Using a Synthetic Trisaccharide Acceptor", Biochem. and Biophys. Res. Commun., vol. 146, No. 2, pp. 679–684, 1987.

R. Cummings et al., "A Mouse Lymphoma Cell Line Resistant to the Leukoagglutinating Lectin from *Phaseolus vulgaris* Is Deficient in UDP–GlcNAc:α–D–mannoside β1,6 N–Acetylglucosaminyltransferase", J. Biol. Chem., vol. 257, No. 22, pp. 13421–13427, 1982.

S. Hiraizumi et al., "Transfection with Fragments of the Adenovirus 12 Gene Induces Tumorigenicity–Associated of N–Linked Sugar Chains in Rat Cells"*Archives of Biochem. and Biophys.*, vol. 280, No. 1, pp. 9–19, Jul. 1990.

J.W. Dennis et al., "Oncodevelopmental Expression of –GlcNacβ1–6Manα1–6Manβ1–Branched Asparagine–linked Oligosaccharides in Murine Tissues and Human Breast Carcinomas", Cancer Res.,vol. 49, pp. 945–950, Feb. 1989.

(List continued on next page.)

*Primary Examiner*—Charles L. Patterson, Jr.
*Attorney, Agent, or Firm*—Burns, Doane, Swecker, Mathis, L.L.P.

[57] ABSTRACT

A β1,6-N-acetylglucosaminyl transferase having the following properties:

(1) Action: it transfers N-acetylglucosamine from UDP-N-acetylglucosamine to α-6-D-mannoside;

(2) Substrate specificity: it shows a reactivity of about 79% for GnGnF-bi-PA, about 125% for GnGnGn-tri-PA and about 66% for GnM-Pa, when taking a reactivity for GnGn-bi-PA as 100%;

(3) Optimum pH: 6.2 to 6.3;

(4) Inhibition, Activation and Stability: $Mn^{2+}$ is not necessary for expression of activity, and the activity is not inhibited in the presence of 20 mM EDTA;

(5) Molecular weight: about 73,000 as determined by SDS-PAGE in the absence of reducing agent; and about 73,000 and about 60,000 as determined in the presence of a reducing agent;

(6) Km value: 133 μM and 3.5 mM for acceptor GnGn-bi-PA and donor UDP-GlcNAc, respectively; and (7) It includes the following peptide fragments:
 (SEQ ID NO.1) Thr-Pro-Trp-Gly-Lys
 (SEQ ID NO.2) Asn-Ile-Pro-Ser-Tyr-Val
 (SEQ ID NO.3) Val-Leu-Asp-Ser-Phe-Gly-Thr-Glu-Pro-Glu-Phe-Asn-His-Ala-Asn-Tyr-Ala
 (SEQ ID NO.4) Asp-Leu-Gln-Phe-Leu-Leu
 (SEQ ID NO.5) Asn-Thr-Asp-Phe-Phe-Ile-Gly,
and gene coding for said enzyme, and a process for production of the enzyme.

10 Claims, 10 Drawing Sheets

OTHER PUBLICATIONS

R. Kumar et al., "Cloning and Expression of N–acetyglucosaminyltransferase I, the Medial Golgi Transferase That Initiates Complex N–linked Carbohydrate Formation", *Proc. Natl. Acad. Sci. USA*, vol. 87, pp. 9948–0052, Dec. 1990.

M. Sarkar et al., "Molecular Cloning and Expression of cDNA encoding the enzyme that controls Conversion of High–mannose to Hybrid and Complex N–glycans: UDP–N–acetylglucoasamine:α–3–D–Mannoside β–1, 2–N–Acetylglucosaminyltransferase 1", *Proc. Natl. Acad. Sci. USA*, vol. 88, pp. 234–238, Jan. 1991.

A. Nishikawa et al., "Determination of N–Acetylglucosaminyltransferase III, IV and V in Normal and Hepatoma Tissues of Rats", *Biochimica et Biophysica Acta*, vol. 1035, pp. 313–318, 1990.

N. Taniguchi et al., "Glycosyltransferase Assys Using Pyridylaminated Acceptors: N–Acetylglucosaminyltransferase III, IV, and V", *Methods Enzymol.*, vol. 179, pp. 397–408, 1989.

M. Redinbaugh, "Adaptation of the Bicinchoninic Acid Protein Assay for Use With Microtiter Plates and Sucrose Gradient Factions", *Analytical Biochemistry*, vol. 153, pp. 267–271, 1986.

Schaechter, H., et al, (1991) Biochem. Soc. Trans 19(3), 645–648.

| pH | ACTIVITY |
|---|---|
| 6.0 | 12.7 (nmol/hr/mg) |
| 6.25 | 15.3 |
| 6.5 | 10.8 |
| 7.0 | 7.8 |

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Thr Pro Trp Gly Lys
    1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Asn Ile Pro Ser Tyr Val
    1                   5

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Val Leu Asp Ser Phe Gly Thr Glu Pro Glu Phe Asn His Ala Asn Tyr
    1               5                        10                   15

Ala ( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Asp Leu Gln Phe Leu Leu
    1                   5

5,707,846

19

20

-continued ( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Asn  Thr  Asp  Phe  Phe  Ile  Gly
    1                      5

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGAATTCTTY AAYCAYGCNA AYTAYGC                                            27

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TTRTGNCTRA ARAARTACTT AAGG                                                24

( 2 ) INFORMATION FOR SEQ ID NO:8:

( i ) SEQUENCE CHARACTERISTICS:
        ( A ) LENGTH: 2095 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 156..2093

( x i ) SEQUENCE DESCRIPTION: SEQ ID NO:8:

CCGGCTGAAG CATCAGAATG GAAGTGAGGA AAGGCAACCA GCTGACACAG GAGCCAGAGT    60

GAGACCAGCA GACTCTCACA CTCAACCTAC ACCATGAATT TGTGTCTATC TTCTACGCGT    120

TAAGAGCCAA GGACAGGTGA AGTTGCCAGA GAGCA ATG GCT CTC TTC ACT CCG    173
                                                        Met Ala Leu Phe Thr Pro
                                                         1                  5

TGG AAG TTG TCC TCT CAG AAG CTG GGC TTT TTC CTG GTG ACT TTT GGC    221
Trp Lys Leu Ser Ser Gln Lys Leu Gly Phe Phe Leu Val Thr Phe Gly
        10                        15                     20

TTC ATT TGG GGT ATG ATG CTT CTG CAC TTT ACC ATC CAG CAG CGA ACT    269
Phe Ile Trp Gly Met Met Leu Leu His Phe Thr Ile Gln Gln Arg Thr
      25                        30                     35

-continued

| | | | | | | | | | | | | | | | | |
|---|---|---|---|---|---|---|---|---|---|---|---|---|---|---|---|---|
| CAG | CCT | GAA | AGC | AGC | TCC | ATG | CTG | CGC | GAG | CAG | ATC | CTG | GAC | CTC | AGC | 317 |
| Gln | Pro | Glu | Ser | Ser | Ser | Met | Leu | Arg | Glu | Gln | Ile | Leu | Asp | Leu | Ser | |
| | 40 | | | | 45 | | | | | 50 | | | | | | |
| AAA | AGG | TAC | ATC | AAG | GCA | CTG | GCA | GAA | GAA | AAC | AGG | AAT | GTG | GTG | GAT | 365 |
| Lys | Arg | Tyr | Ile | Lys | Ala | Leu | Ala | Glu | Glu | Asn | Arg | Asn | Val | Val | Asp | |
| 55 | | | | 60 | | | | | 65 | | | | | | 70 | |
| GGG | CCA | TAC | GCT | GGA | GTC | ATG | ACA | GCT | TAT | GAT | CTG | AAG | AAA | ACC | CTT | 413 |
| Gly | Pro | Tyr | Ala | Gly | Val | Met | Thr | Ala | Tyr | Asp | Leu | Lys | Lys | Thr | Leu | |
| | | | | 75 | | | | 80 | | | | | 85 | | | |
| GCT | GTG | TTA | TTA | GAT | AAC | ATT | TTG | CAG | CGC | ATT | GGC | AAG | TTG | GAG | TCG | 461 |
| Ala | Val | Leu | Leu | Asp | Asn | Ile | Leu | Gln | Arg | Ile | Gly | Lys | Leu | Glu | Ser | |
| | | | 90 | | | | | 95 | | | | 100 | | | | |
| AAG | GTG | GAC | AAT | CTT | GTT | GTC | AAT | GGC | ACC | GGA | ACA | AAC | TCA | ACC | AAC | 509 |
| Lys | Val | Asp | Asn | Leu | Val | Val | Asn | Gly | Thr | Gly | Thr | Asn | Ser | Thr | Asn | |
| | | 105 | | | | | 110 | | | | | 115 | | | | |
| TCC | ACT | ACA | GCT | GTT | CCC | AGC | TTG | GTT | GCA | CTT | GAG | AAA | ATT | AAT | GTG | 557 |
| Ser | Thr | Thr | Ala | Val | Pro | Ser | Leu | Val | Ala | Leu | Glu | Lys | Ile | Asn | Val | |
| | 120 | | | | | 125 | | | | | 130 | | | | | |
| GCA | GAT | ATC | ATT | AAC | GGA | GCT | CAA | GAA | AAA | TGT | GTA | TTG | CCT | CCT | ATG | 605 |
| Ala | Asp | Ile | Ile | Asn | Gly | Ala | Gln | Glu | Lys | Cys | Val | Leu | Pro | Pro | Met | |
| 135 | | | | | 140 | | | | | 145 | | | | | 150 | |
| GAC | GGC | TAC | CCT | CAC | TGT | GAG | GGA | AAG | ATC | AAG | TGG | ATG | AAA | GAC | ATG | 653 |
| Asp | Gly | Tyr | Pro | His | Cys | Glu | Gly | Lys | Ile | Lys | Trp | Met | Lys | Asp | Met | |
| | | | | 155 | | | | | 160 | | | | | 165 | | |
| TGG | CGT | TCA | GAT | CCC | TGC | TAC | GCA | GAC | TAT | GGA | GTG | GAT | GGA | TCC | ACC | 701 |
| Trp | Arg | Ser | Asp | Pro | Cys | Tyr | Ala | Asp | Tyr | Gly | Val | Asp | Gly | Ser | Thr | |
| | | | 170 | | | | | 175 | | | | | 180 | | | |
| TGC | TCT | TTT | TTT | ATT | TAC | CTC | AGT | GAG | GTT | GAA | AAT | TGG | TGT | CCT | CAT | 749 |
| Cys | Ser | Phe | Phe | Ile | Tyr | Leu | Ser | Glu | Val | Glu | Asn | Trp | Cys | Pro | His | |
| | | 185 | | | | | 190 | | | | | 195 | | | | |
| TTA | CCT | TGG | AGA | GCA | AAA | AAT | CCC | TAC | GAA | GAA | GCT | GAT | CAT | AAT | TCA | 797 |
| Leu | Pro | Trp | Arg | Ala | Lys | Asn | Pro | Tyr | Glu | Glu | Ala | Asp | His | Asn | Ser | |
| | 200 | | | | | 205 | | | | | 210 | | | | | |
| TTG | GCG | GAA | ATT | CGT | ACA | GAT | TTT | AAT | ATT | CTC | TAC | AGT | ATG | ATG | AAA | 845 |
| Leu | Ala | Glu | Ile | Arg | Thr | Asp | Phe | Asn | Ile | Leu | Tyr | Ser | Met | Met | Lys | |
| 215 | | | | | 220 | | | | | 225 | | | | | 230 | |
| AAG | CAT | GAA | GAA | TTC | CGG | TGG | ATG | AGA | CTA | CGG | ATC | CGG | CGA | ATG | GCT | 893 |
| Lys | His | Glu | Glu | Phe | Arg | Trp | Met | Arg | Leu | Arg | Ile | Arg | Arg | Met | Ala | |
| | | | | 235 | | | | | 240 | | | | | 245 | | |
| GAC | GCA | TGG | ATC | CAA | GCA | ATC | AAG | TCC | CTG | GCA | GAA | AAG | CAG | AAC | CTT | 941 |
| Asp | Ala | Trp | Ile | Gln | Ala | Ile | Lys | Ser | Leu | Ala | Glu | Lys | Gln | Asn | Leu | |
| | | | 250 | | | | | 255 | | | | | 260 | | | |
| GAA | AAG | AGA | AAG | CGG | AAG | AAA | GTC | CTC | GTT | CAC | CTG | GGA | CTC | CTG | ACC | 989 |
| Glu | Lys | Arg | Lys | Arg | Lys | Lys | Val | Leu | Val | His | Leu | Gly | Leu | Leu | Thr | |
| | | 265 | | | | | 270 | | | | | 275 | | | | |
| AAG | GAA | TCT | GGA | TTT | AAG | ATT | GCA | GAG | ACA | GCT | TTC | AGT | GGT | GGC | CCT | 1037 |
| Lys | Glu | Ser | Gly | Phe | Lys | Ile | Ala | Glu | Thr | Ala | Phe | Ser | Gly | Gly | Pro | |
| | 280 | | | | | 285 | | | | | 290 | | | | | |
| CTT | GGT | GAA | TTA | GTT | CAA | TGG | AGT | GAT | TTA | ATT | ACA | TCT | CTG | TAC | TTA | 1085 |
| Leu | Gly | Glu | Leu | Val | Gln | Trp | Ser | Asp | Leu | Ile | Thr | Ser | Leu | Tyr | Leu | |
| 295 | | | | | 300 | | | | | 305 | | | | | 310 | |
| CTG | GGC | CAT | GAC | ATT | AGG | ATT | TCA | GCT | TCA | CTG | GCT | GAG | CTC | AAG | GAA | 1133 |
| Leu | Gly | His | Asp | Ile | Arg | Ile | Ser | Ala | Ser | Leu | Ala | Glu | Leu | Lys | Glu | |
| | | | | 315 | | | | | 320 | | | | | 325 | | |
| ATC | ATG | AAG | AAG | GTT | GTA | GGA | AAC | CGA | TCT | GGC | TGC | CCA | ACT | GTA | GGA | 1181 |
| Ile | Met | Lys | Lys | Val | Val | Gly | Asn | Arg | Ser | Gly | Cys | Pro | Thr | Val | Gly | |
| | | | 330 | | | | | 335 | | | | | 340 | | | |
| GAC | AGA | ATT | GTT | GAG | CTC | ATT | TAC | ATT | GAT | ATT | GTA | GGA | CTT | GCT | CAA | 1229 |
| Asp | Arg | Ile | Val | Glu | Leu | Ile | Tyr | Ile | Asp | Ile | Val | Gly | Leu | Ala | Gln | |
| | | | 345 | | | | | 350 | | | | | 355 | | | |

| | | | | | | | | | | | | | | | | |
|---|---|---|---|---|---|---|---|---|---|---|---|---|---|---|---|---|
| TTC | AAG | AAA | ACT | CTT | GGA | CCA | TCC | TGG | GTT | CAT | TAC | CAG | TGC | ATG | CTC | 1277 |
| Phe | Lys | Lys | Thr | Leu | Gly | Pro | Ser | Trp | Val | His | Tyr | Gln | Cys | Met | Leu | |
| | 360 | | | | | 365 | | | | | 370 | | | | | |
| CGA | GTC | CTT | GAT | TCA | TTT | GGT | ACT | GAA | CCC | GAA | TTT | AAT | CAT | GCA | AAT | 1325 |
| Arg | Val | Leu | Asp | Ser | Phe | Gly | Thr | Glu | Pro | Glu | Phe | Asn | His | Ala | Asn | |
| 375 | | | | | 380 | | | | | 385 | | | | | 390 | |
| TAT | GCC | CAA | TCG | AAA | GGC | CAC | AAG | ACC | CCT | TGG | GGA | AAA | TGG | AAT | CTG | 1373 |
| Tyr | Ala | Gln | Ser | Lys | Gly | His | Lys | Thr | Pro | Trp | Gly | Lys | Trp | Asn | Leu | |
| | | | | 395 | | | | | 400 | | | | | 405 | | |
| AAC | CCT | CAG | CAG | TTT | TAT | ACC | ATG | TTC | CCT | CAT | ACC | CCA | GAC | AAC | AGC | 1421 |
| Asn | Pro | Gln | Gln | Phe | Tyr | Thr | Met | Phe | Pro | His | Thr | Pro | Asp | Asn | Ser | |
| | | | 410 | | | | | 415 | | | | | 420 | | | |
| TTT | CTG | GGG | TTT | GTG | GTT | GAG | CAG | CAC | CTG | AAC | TCC | AGT | GAT | ATC | CAC | 1469 |
| Phe | Leu | Gly | Phe | Val | Val | Glu | Gln | His | Leu | Asn | Ser | Ser | Asp | Ile | His | |
| | | 425 | | | | | 430 | | | | | 435 | | | | |
| CAC | ATT | AAT | GAA | ATC | AAA | AGG | CAG | AAC | CAG | TCC | CTT | GTG | TAT | GGC | AAA | 1517 |
| His | Ile | Asn | Glu | Ile | Lys | Arg | Gln | Asn | Gln | Ser | Leu | Val | Tyr | Gly | Lys | |
| | 440 | | | | | 445 | | | | | 450 | | | | | |
| GTG | GAT | AGC | TTC | TGG | AAG | AAT | AAG | AAG | ATC | TAC | TTG | GAC | ATT | ATT | CAC | 1565 |
| Val | Asp | Ser | Phe | Trp | Lys | Asn | Lys | Lys | Ile | Tyr | Leu | Asp | Ile | Ile | His | |
| 455 | | | | | 460 | | | | | 465 | | | | | 470 | |
| ACA | TAC | ATG | GAA | GTG | CAT | GCA | ACT | GTT | TAT | GGC | TCC | AGC | ACA | AAG | AAT | 1613 |
| Thr | Tyr | Met | Glu | Val | His | Ala | Thr | Val | Tyr | Gly | Ser | Ser | Thr | Lys | Asn | |
| | | | | 475 | | | | | 480 | | | | | 485 | | |
| ATT | CCC | AGT | TAC | GTG | AAA | AAC | CAT | GGT | ATC | CTC | AGT | GGA | CGG | GAC | CTG | 1661 |
| Ile | Pro | Ser | Tyr | Val | Lys | Asn | His | Gly | Ile | Leu | Ser | Gly | Arg | Asp | Leu | |
| | | | 490 | | | | | 495 | | | | | 500 | | | |
| CAG | TTC | CTT | CTT | CGA | GAA | ACC | AAG | TTG | TTT | GTT | GGA | CTT | GGG | TTC | CCT | 1709 |
| Gln | Phe | Leu | Leu | Arg | Glu | Thr | Lys | Leu | Phe | Val | Gly | Leu | Gly | Phe | Pro | |
| | | 505 | | | | | 510 | | | | | 515 | | | | |
| TAC | GAG | GGC | CCA | GCT | CCC | CTG | GAA | GCT | ATC | GCA | AAT | GGA | TGT | GCT | TTT | 1757 |
| Tyr | Glu | Gly | Pro | Ala | Pro | Leu | Glu | Ala | Ile | Ala | Asn | Gly | Cys | Ala | Phe | |
| | 520 | | | | | 525 | | | | | 530 | | | | | |
| CTG | AAT | CCC | AAG | TTC | AAC | CCA | CCC | AAA | AGC | AGC | AAA | AAC | ACA | GAC | TTT | 1805 |
| Leu | Asn | Pro | Lys | Phe | Asn | Pro | Pro | Lys | Ser | Ser | Lys | Asn | Thr | Asp | Phe | |
| 535 | | | | | 540 | | | | | 545 | | | | | 550 | |
| TTC | ATT | GGC | AAG | CCA | ACT | CTG | AGA | GAG | CTG | ACA | TCC | CAG | CAT | CCT | TAC | 1853 |
| Phe | Ile | Gly | Lys | Pro | Thr | Leu | Arg | Glu | Leu | Thr | Ser | Gln | His | Pro | Tyr | |
| | | | | 555 | | | | | 560 | | | | | 565 | | |
| GCT | GAA | GTT | TTC | ATC | GGG | CGG | CCA | CAT | GTG | TGG | ACT | GTT | GAC | CTC | AAC | 1901 |
| Ala | Glu | Val | Phe | Ile | Gly | Arg | Pro | His | Val | Trp | Thr | Val | Asp | Leu | Asn | |
| | | | 570 | | | | | 575 | | | | | 580 | | | |
| AAT | CAG | GAG | GAA | GTA | GAG | GAT | GCA | GTG | AAA | GCA | ATT | TTA | AAT | CAG | AAG | 1949 |
| Asn | Gln | Glu | Glu | Val | Glu | Asp | Ala | Val | Lys | Ala | Ile | Leu | Asn | Gln | Lys | |
| | | 585 | | | | | 590 | | | | | 595 | | | | |
| ATT | GAG | CCA | TAC | ATG | CCA | TAT | GAA | TTT | ACG | TGC | GAG | GGG | ATG | CTA | CAG | 1997 |
| Ile | Glu | Pro | Tyr | Met | Pro | Tyr | Glu | Phe | Thr | Cys | Glu | Gly | Met | Leu | Gln | |
| | 600 | | | | | 605 | | | | | 610 | | | | | |
| AGA | ATC | AAT | GCT | TTC | ATT | GAA | AAA | CAG | GAC | TTC | TGC | CAT | GGG | CAA | GTG | 2045 |
| Arg | Ile | Asn | Ala | Phe | Ile | Glu | Lys | Gln | Asp | Phe | Cys | His | Gly | Gln | Val | |
| 615 | | | | | 620 | | | | | 625 | | | | | 630 | |
| ATG | TGG | CCA | CCC | CTC | AGC | GCC | CTA | CAG | GTC | AAG | CTT | GCT | GAG | CCC | GGG | 2093 |
| Met | Trp | Pro | Pro | Leu | Ser | Ala | Leu | Gln | Val | Lys | Leu | Ala | Glu | Pro | Gly | |
| | | | | 635 | | | | | 640 | | | | | 645 | | |
| CC | | | | | | | | | | | | | | | | 2095 |

( 2 ) INFORMATION FOR SEQ ID NO:9:

( i ) SEQUENCE CHARACTERISTICS:
        ( A ) LENGTH: 7 amino acids
        ( B ) TYPE: amino acid

```
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..7
            ( D ) OTHER INFORMATION: /note="Amino acid sequence encoded
                  by nucleotides 8-27 of SEQ ID NO. 6."

( x i ) SEQUENCE DESCRIPTION: SEQ ID NO:9:

Phe  Asn  His  Ala  Asn  Tyr  Ala
    1                   5

( 2 ) INFORMATION FOR SEQ ID NO:10:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..5
            ( D ) OTHER INFORMATION: /note="Amino acid sequence
                  encoded by nucleotides 1-15 of SEQ ID NO. 7."

( x i ) SEQUENCE DESCRIPTION: SEQ ID NO:10:

Asn  Thr  Asp  Phe  Phe
    1                   5
```

N-ACETYLGLUCOSAMINYL TRANSFERASE GENE CODING THEREFOR AND PROCESS FOR PRODUCTION THEREOF

This application is a divisional of application Ser. No. 08/110,736, filed Aug. 23, 1993.

BACKGROUND OF THE INVENTION

1. Field of the Invention

The present invention relates to an enzyme which transfers N-acetylglucosamine from UDP-N-acetylglucosamine to α-6-D-mannoside (UDP-N-Acetylglucosamine: α-6-D-Mannoside β1-6N-Acetylglucosaminyl transferase; N-Acetylglucosaminyltransferase; hereinafter abbreviated as GnT-V), a gene coding therefor, and a process for production of GnT-V.

2. Description of Related Art

Asparagine type sugar chains found in glycoproteins are classified as three types, i.e., high mannose type, complex type and mixed type on the basis of constituent sugars and the types of branching. Biosynthesis of these Asn type sugar chains is first started with transfer of all sugar chain moieties of a lipid intermediate from the lipid intermediate to asparagine of a polypeptide chain during translation thereof in the lumina of the rough-surfaced endoplasmic reticulum.

After that glucose and a portion of mannose are removed in the rough-surfaced endoplasmic reticulum. However, a portion of glycoprotein having Asn type sugar chains located in the rough-surfaced endoplasmic reticulum remains there intact, and retains the mannose type sugar chain. Other organella glycoproteins, cell surface glycoproteins or secretory glycoproteins are transferred to the Golgi body by Golgi transportation, and mannose is removed. In the Golgi body, Golgi body enzymes, N-acetylglucosaminyl transferases, introduces N-acetylglucosamine and branching structure is formed. By the formation of this branching structure, conversion of high mannose type sugar chain to mixed type sugar chain and complex sugar chain starts, and through the introduction of fucose and then of galactose in the trans Golgi region, and finally, introduction of sialic acid biosynthesis of Asn type sugar chain is completed.

In the steps of the formation of Asn-type sugar chains, it has been found that various enzymes catalyze the reaction. Among them, as enzymes catalyzing the transfer of N-acetylglucosamine, 6 kinds of N-acetylglucosaminyl transferases are known. Schachter et al., Brockausen, I. Caarver, J., and Schachter, H., Biochem. Cell. Biol., 66, 1134 (1988) named the six enzymes which transfer N-acetylglucosamine to the core structure of trimannosyl structure, Manα1-3(Manα1-6) Manβ1-4GlcNAcβ1-4GlcNAc as GnT-1 through GnT-VI.

Among them, the GnT-V is an enzyme participating in the formation of a β(1,6) branch structure (-[GlcNAc-β(1,6) Man-α(1,6)Man]-). It is known that the β(1,6) branch structure increases in transformed cells and tumorigenic cells (Pierce, M., Arango, J., Tahir, S. H. and Hindsgunl, O., Biochem. Biophs. Res. Commun., 146, 679–684 (1987) and Arango, J. and Pierce, M., J. Cell. Biochem. 257, 13421–13427 (1982)).

Moreover, it was shown that the metastatic ability of tumorigenic cells correlates with the occurrence of β(1,6) branch (Hiraizumi, S., Takasaki, S., Shiroki, K., Kochibe, N., and Kobata, H., Arch. Biochem. Biophys. 280, 9–19 (1990)). In biopsies of human breast cancer, reportedly, in 50% of the cases the expression of the β(1,6) branch was accelerated (Dennis, J. W., and Laferrte, S. Cancer Res. 49, 945–950 (1989)).

In any case, it is known that the occurrence of β(1,6) branch structure is accompanied with an increase of GnT-V activity. As seen from the above, the GnT-V is not only important in that it catalyses formation of the β(1,6) branch structure in the biosynthesis of sugar chain, but is also important in that it is related to detection of the metastatic ability and the degree of malignancy of cancer cells.

Among these six N-acetylglucosaminyl transferases, human and rabbit cDNA structures for GnT-I were clarified (Kumar, R., Yang, J., Larsen, R. C., and Stanley, P. Procc. Natl. Acad. Sci. USA, 87, 9948–9952 (1990) and Sarkev, M. Hull, E., Nishikawa, Y., Simpson, R. J., Noritz, R. L., Dunn, R., and Schachter, H., Proc. Natl. Acad. Sci. U.S.A 88 234–238 (1991).

On the other hand, the presence of GnT-V was predicted from its enzyme activity, and its purification from various tissues was attempted, but it was very difficult (Nishikawa, A., Gu, J., Fujii, S., and Taniguchi, N. Biochem. Biophys. Acta 103, 313–318 (1990)). However, recently, isolation and purification of GnT-V from rat kidney was reported (Shoreibah, M., G., Handgaul, O., and Picerce, M., J. Biol. Chem. 267, 2920–2927 (1992)).

However, detailed information relating to the gene of said enzyme has not been obtained from rat GnT-V. For human GnT-V, any information including its enzymatic characteristics is not available. Not only is GnT-V very effective for diagnosis as a marker for the degree of malignancy of cancer cells, but also it will be useful in that it will make it possible to design a metastasis inhibitory agent by establishing a screening system for specific inhibitor. Therefore, it is desired to isolate and purify GnT-V of human origin, and to analyze the structures including the gene and to produce it in a large amount.

SUMMARY OF THE INVENTION

Accordingly, in one aspect, the present invention provides GnT-V of human origin. In addition, according to the present invention the gene for the present enzyme is isolated, a process for a large scale production of the enzyme using said gene is developed, and formation of homogeneous sugar chains in the production of a desired product by gene engineering becomes possible.

The present inventors noted a supernatant of cancer cells as a starting material for purification of the present enzyme. However, the present inventors also noted that purification of the enzyme was difficult in the use of a culture supernatant of cancer cells which can grow only in the presence of bovine serum or the like. Accordingly, the present inventors tried to condition various cancer cells for growth in protein-free medium, and succeeded in establishing tens of cancer cells conditioned to protein-free media. Among them, the present inventor detected an activity of the present enzyme in a culture supernatant from protein-free medium in which QG cells derived from human lung carcinoma (small cell cancer) were cultured, and succeeded in purifying the present enzyme.

Accordingly, the present invention provide a β1,6-N-acetylglucosaminyl transferase having the following properties:

(1) Action: it transfers N-acetylglucosamine from UDP-N-acetylglucosamine to α-6-D-mannoside;

(2) Substrate specificity: it shows a reactivity of about 78% for GnGnF-bi-PA, about 125% for GnGnGn-tri-PA and about 66% for GnM-PA, when taking a reactivity for GnGn-bi-PA acceptor as 100%;

(3) Optimum pH: 6.2 to 6.3;

(4) Inhibition, Activation and Stability: $Mn^{2+}$ is not necessary for expression of activity, and the activity is not inhibited in the presence of 20 mM EDTA;

(5) Molecular weight: about 73,000 as determined by SDS-PAGE in the absence of reducing agent; and about 73,000 and about 60,000 as determined in the presence of a reducing agent;

(6) Km value: 133 µM and 3.5 mM for acceptor GnGn-bi-PA (GlcNAcβ1-2 Man α1-3-(GlcNAcβ1-2 Man α1-6) (Man β1-4 GlcNAcβ1-4 GlcNAc-2-aminopyridine); and donor UDP-GlcNAc(uridine-5'-diphospho-N-acetylglucosamine), respectively; and (7) It includes the following peptide fragments:

(SEQ ID NO:1) Thr-Pro-Trp-Gly-Lys (SEQ ID NO:2) Asn-Ile-Pro-Ser-Tyr-Val (SEQ ID NO:3) Val-Leu-Asp-Ser-Phe-Gly-Thr-Glu-Pro-Glu-Phe-Asn-His-Ala-Asn-Tyr-Ala (SEQ ID NO:4) Asp-Leu-Gln-Phe-Leu-Leu (SEQ ID NO:5) Asn-Thr-Asp-Phe-Phe-Ile-Gly

The present enzyme β1,6-N-acetylglucosaminyl transferase comprises, for example, an amino acid sequence comprising the amino acid sequence shown in SEQ ID No: 8, or an amino acid sequence wherein one or more than one amino acid residue is modified in the amino acid sequence shown in SEQ ID No: 8. Herein, the amino acid modification means that one or more amino acid residues are added, deleted and/or replaced with other amino acids.

The present invention further provides a process for production of the above-mentioned enzyme comprising the steps of culturing QG cells derived from human lung carcinoma, and recovering said enzyme from the culture.

The present invention still further provides a process for production of the above-mentioned enzyme comprising the steps of culturing or raising a host transformed with a DNA coding for said enzyme, and recovering the enzyme from the culture or raised host.

The present invention also relates to gene system encoding the enzyme i.e., DNA, expression vectors and transformed host.

PREFERRED EMBODIMENT FOR CARRYING OUT THE INVENTION

Figure 1:
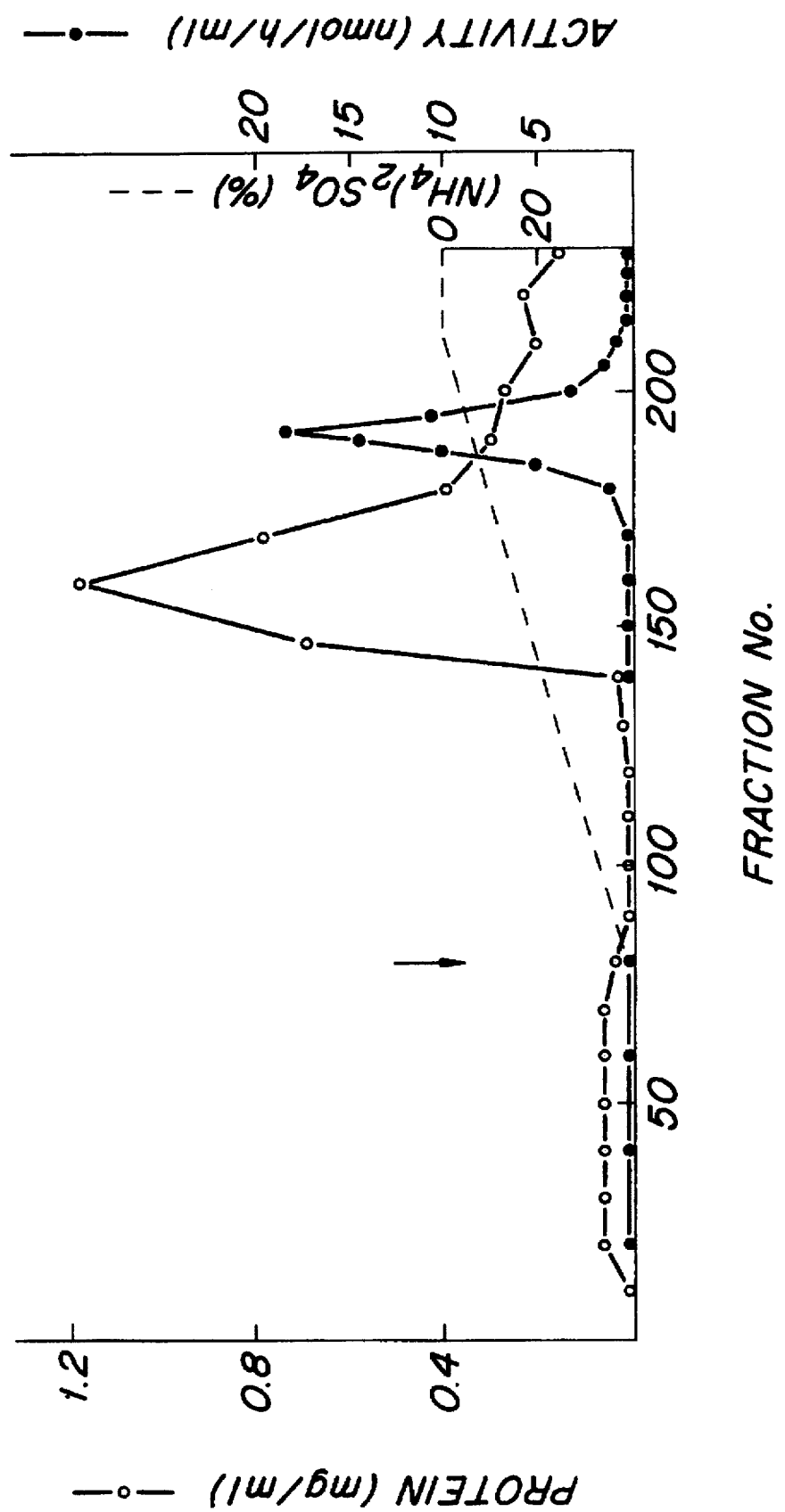
FIG. 1 shows an elution profile of Phenyl-Sepharose column chromatography, wherein solid circles linked with solid lines show GnT-V activity. The elution was carried out by decreasing concentration of ammonium sulfate from 40% to 0%. Concentration of ammonium sulfate is shown by a broken line.

QG cells derived from human lung carcinoma cells (small cell cancer) can be cultured by any method conventionally used for culturing animal cells. The QG cells can be cultured by static culture in a protein free medium, that is, the medium is not supplemented with any extrageneous proteins. Note, a culture of the QG cells derived from human lung carcinoma (small cell cancer) was designated as Human lung carcinoma SBM331 and deposited with Fermentation Research Institute Agency of Industrial Science and Technology, 1-3 Higashi 1-chome, Tsukuba-shi, Ibaraki-ken, 305, Japan, as FERM BP-3967 on Aug. 18, 1992, under Budapest Treaty.

An enzyme activity can be easily assayed by labeling an acceptor with a radioisotope or with fluorescent substance, adding the enzyme and separating the reaction product by high performance liquid chromatography (HPLC). More specifically, the method reported by Tanigichi et al. (Taniguchi, N., Nishikawa, A., Fujii, S., and Gu. J., Methods Enzymol. 179, 397–408 (1989); Nishikawa, H., Gu, J., Fujii, S., and Tanigichi, N., Biochem. Biophys. Acta, 1035, 313–318 (1990)) may be followed.

Namely, the enzyme activity of GnT-V can be assayed using GnGn-2-aminopyridine (GnGn-bi-PA) as an acceptor, and UDP-GluNAc (Sigma) as a donor. Activity is shown by an amount of transferred N-acetylglucosamine/hour/mg protein. Note, an amount of protein can be measured according to a reported method (Redinbaugh, M. G., and Turley, R. B., Anal. Biochem. 153, 267–271 (1986)) using a BCA kit (Pierce Chemical Company, Rockford, Ill.) and using bovine serum albumin as a standard.

The present enzyme can be isolated and purified by using procedures singly or in combination conventionally used for purification of a protein. In addition, as a useful purification method for the present enzyme, an affinity of the enzyme to an acceptor or donor can be used. According to one embodiment of the present invention, a culture supernatant from a protein-free culture is first concentrated by ultrafiltration, and an active fraction is obtained by hydrophobic chromatography using Phenyl-Sepharose.

Next, after absorption to Hydroxylapatite, an active fraction is eluted, and the active fraction is subjected to acceptor column chromatography (UDP-hexanolamine-Agarose) and donor column chromatography (GnGn-Asn-Sepharose), followed by sodium dodecyl sulfate-polyacrylamide gel electrophoresis in the absence of reducing agent to obtain a polypeptide showing a single band.

A particular example for the purification is described in Example 2. As seen from Example 2, the present inventors succeeded in isolating and purifying a 20,000-fold purified GnT-V by 4-step purification procedure from the above-mentioned culture supernatant concentrate of protein-free culture, and determined partial amino acid sequences of the enzyme. The enzyme of the present invention was obtained for the first time by a particular combination of procedures used for isolation and purification of a protein, under particular conditions.

Once the present enzyme was isolated and purified, and structural properties of the enzyme were clarified as described hereinafter, the present enzyme can be isolated and purified using the known properties as an indicator according to any other combination of conventional procedures used for isolation and purification of a protein. Moreover, synthetic probes can be prepared on the basis of partial amino acid sequences of the present enzyme disclosed herein, genomic library and cDNA library derived from avian, amphibia, mammal and the like can be screened with said probes to isolate genes, and the gene can be used to produce a corresponding enzyme.

An enzyme isolated and purified according to the present invention has the following properties.

1. Action: it transfers N-acetylglucosamine from UDP-N-acetylglucosamine to α-6-D-mannoside;

2. Substrate specificity: it shows a reactivity of about 78% for GnGnF-bi-PA, about 125% for GmGmGm-tri-PA, and about 66% for GnM-PA, when taking a reactivity for GnGn-bi-PA acceptor as 100%;

3. Optimum pH for reaction: 6.2 to 6.3;

4. Inhibition, Activation and Stability: $Mn^{2+}$ is not necessary for expression of the activity, and the activity is not inhibited in the presence of 20 mM EDTA;

5. Molecular weight: as a result obtained by sodium dodecyl sulfate-polyacrylamide gel electrophoresis (SDS-PAGE), it shows a single band corresponding to a molecular weight of about 73,000 under a non-reducing condition, and it shows a band corresponding to a lower molecular weight of about 60,000 in addition to the above-mentioned band of about 73,000. In addition, when the isolated and purified enzyme is subjected to native polyacrylamide gel electrophoresis, the extraction samples from the sections of the native polyacrylamide gel exhibit the enzyme activity in a density dependent manner. From the above result, the isolated and purified protein is confirmed to be the desired GnT-V. A particular result is described in Example 3.

On the other hand, two bands in an SDS-polyacrylamide gel electrophoresis under the reducing condition are excised from the gel, and each fraction is digested with trypsin followed by reverse phase high performance liquid chromatography and peptide mapping. As a result, both the 60 kDa fraction and 73 kDa fractions show similar elution paterns. From this result, it is concluded that both the proteins are derived from the same protein even though there is possibility that one of or both the enzymes have been enzymatically cleaved;

6. Km value: 133 μM and 3.5 mM for acceptor GG-bi-PA and donor UDP-GlcNAc, respectively; and 7. Peptide fragments: amino acid sequences of peptide fragments obtained by digestion of the enzyme with trypsin are as follows:

(SEQ ID NO:1). Thr-Pro-Trp-Gly-Lys (SEQ ID NO:2) Asn-Ile-Pro-Ser-Tyr-Val (SEQ ID NO:3) Val-Leu-Asp-Ser-Phe-Gly-Thr-Glu-Pro-Glu-Phe-Asn-His-Ala-Asn-Tyr-Ala (SEQ ID NO:4) Asp-Leu-Gln-Phe-Leu-Leu (SEQ ID NO:5) Asn-Thr-Asp-Phe-Phe-Ile-Gly

Further, a gene coding for GnT-V of the present invention can be obtained by preparing oligonucleotide probes on the basis of the amino acid sequences of the peptide fragments and screening a genomic library or a cDNA library using the probes.

Gene of the present invention may be cDNA, genomic DNA and chemically synthesized DNA. For example, cDNA can be cloned by polymerase chain reaction (PCR) using nucleotide primers designed on the basis of the partial amino acid sequences, as shown in Example 5, of GnT-V purified from human cells such as QG cells derived from human lung carcinoma. A particular embodiment of the cloning is shown in Example 8.

The present gene further includes DNA which codes for a protein having GnT-V activity and which hybridizes with the nucleotide sequence shown in Example 8.

A nucleotide sequence of DNA coding for the present GnT-V and cloned in Example 8, and an amino acid sequence predicted from the nucleotide sequence are shown in SEQ ID No: 8.

Thus, once an amino acid sequence is determined, various modified GnT-V, such as polypeptide wherein one or more amino acids are added to the above-mentioned native amino acid sequence and still maintains GnT-V activity, a polypeptide wherein one or more amino acids are deleted from the native amino acid sequence and still maintains GnT-V activity, a polypeptide wherein one or more amino acids are replaced with other amino acids in the native amino acid sequence and still maintains GnT-V activity, and a polypeptide including any combination of the above-mentioned amino acid addition modification, amino acid deletion modification and amino acid replacement modification, can be designed and produced.

Although the number of amino acids in the above-mentioned amino acid addition, deletion or replacement modification is not limited to a particular number, for example, for the addition modification, the number depends on the purposes of the modification, for example, depends on the number of amino acids of a functional protein used for formation of a hybride protein with the present GnT-V (for example, known proteins for purification or stabilization such as maltose-binding protein, or various biologically active proteins for example cytokines such as IL-3, IL-11), or signal peptide attached to the present protein. For example, the number of added amino acids can be 1 to 30, preferably 1 to 10.

For the deletion modification, the number of deleted amino acids is designed and determined so that the modified protein maintains GnT-V activity, and is for example 1 to 30, preferably 1 to 20, or the number of amino acids in regions other than an active region. For the replacement modification, the number of replaced amino acids is designed and determined so that the modified protein maintains GnT-V activity, and is for example 1 to 10, preferably 1 to 5.

According to the present invention, although the nucleotide sequence is shown in SEQ ID No: 8 as a nucleotide sequence coding for GnT-V, the gene of the present invention coding for GnT-V is not limited to it. Once an amino acid sequence of native GnT-V or an amino acid sequence of modified GnT-V is determined, various nucleotide sequences coding for the same amino acid sequence by different codons on the basis of the degeneracy of genetic codons can be designed and prepared. In this case, codons used with a high frequency in a chosen host are preferably used.

Although cDNA can be obtained as a gene coding for the native GnT-V of the present invention, as described in Example 8, it is not limited thereto. Namely, once a nucleotide sequence coding for an amino acid sequence of the native GnT-V is determined, a gene coding for the native GnT-V can be cloned by a strategy different from the strategy specifically described herein; and also, can be cloned from the genome of cells producing the native GnT-V.

Where a gene is cloned from the genome, various primer nucleotides or probe nucleotides used in Example 8 may be used as probes for screening genomic DNA fragments. Moreover, other probes designed on the basis of the nucleotide sequence shown in SEQ ID No: 8 may be used. General procedure for cloning a desired DNA from genome is well known in the art (Current Protocols in Molecular Biology, John Wiley and Sons, Chapters 5 and 6).

In addition gene coding for a native GnT-V of the present invention can be prepared by chemical synthesis. Chemical synthesis of DNA can be easily carried out using an automated DNA synthesizer conventionally used in the art, such as a 396 DNA/RNA synthesizer (Applied Biosystems). Accordingly, a person with ordinary skill in the art can easily synthesize the nucleotide sequence shown in SEQ ID No: 8.

A gene coding for a native GnT-V of the present invention by codons different from native codons can be chemically synthesized as described above, and further can be obtained by a conventional procedure such as site-directed mutagenesis using a DNA or RNA having the nucleotide sequence shown in SEQ ID No: 8 as a templete in combination with a mutagenic primer (see, for example, Current Protocols In Molecular Biology, John Wiley & Sons, Chapter 8).

Once a gene coding for a GnT-V of the present invention is cloned, the gene can be used to produce a recombinant GnT-V according to a conventional gene recombination technique. Namely, a DNA encoding a GnT-V of the present invention is inserted into an adequate vector, and the vector is introduced into an adequate host, and the host is cultured or raised, and the GnT-V is recovered from the culture (cells or medium) or the raised host.

As a host, a prokaryote or eukaryote can be used. As prokaryote, bacteria, especially *Escherichia coli*, Bacillus, such as *B. subfilis* may be used. As eukaryote, eukaryotic microorganisms, for example, yeast such as the genus Succharomyces, such as *S. serevisiae*, insect cells such as cells of *Spodoptera frugiperda*, cells of *Trichoplusia ni* or cells of *Bombyx mori*, animal cells such as human cells, monkey cells, mouse cells can be used. According to the present invention, an insect per se., such as *Bombyx mori*, *Trichoplusia hi*, or the like can be used.

As expression vectors, plasmid, phage, phagemid, virus (baculovirus for insect, vaccinia virus for animal cells) and the like can be used. A promoter in an expression vector is selected depending on the host. For example, as bacterial promoters, for example, lac promoter, trp promoter and the like are used; and as yeast promoters, for example, adh1 promoter, pqk promoter and the like are used. As promoters for insect, for example, baculovirus polyhedrin promoter and the like can be used, and as promoters for animal cells, for example, early or late promoter for Simian virus 40 and the like may be used.

Transformation of a host with an expression vector can be carried out according to conventional procedures well known in the art, and these procedure are described in Current Protocols in Molecular Biology, John Wiley & Sons. Transformants can be cultured according to conventional procedures.

Purification of GnT-V from a culture can be carried out according to a conventional procedure for isolation and purification of a protein, for example, using ultrafiltration, various column chromatography such as Sepharose chromatography.

EXAMPLES

Next, the present invention is further explained by but not limited to the following examples.

Example 1

Culturing of GnT-V producing cells and preparation of culture supernatant

QG cells (FFRM BP-3967) derived from human lung carcinoma (small cell cancer) were cultured in an opticell 5300 (Charles River Inc. Wilmington, Mass.). $2 \times 10^9$ cells were inoculated to a porous ceramic growing chamber (effective surface >32,000 cm$^2$), and grown to a confluent state using Ham's F-12 medium (Flow) containing 5% bovine serum (GIBCO).

Next, protein-free Ham's F-12 medium containing $10^{-8}$M sodium selenite was continuously added to gradually decrease an amount of serum. After culturing for 2 weeks, 140 L of a culture supernatant was obtained. This culture supernatant was concentrated by about 100 fold using an ultrafiltration apparatus equipped with a UF-membrane (Milipore, Bedford, Mass.). 1.4 L of the concentrated supernatant was used as a starting material for purification.

Example 2

Purification of enzyme from the concentrated culture supernatant (1) Preparation of UDP-hexanolamine agarose and GlcNAcβ1-2Manα1-3-(GlcNAcβ1-2Manα1-6) Manβ1-4GlcNAcβ1-4GlcNAc-asparagine (GnGn-Asn) Sepharose UDP-hexanolamine Agarose was purchased from Sigma (St. Louis, Mo.). GnGn-Asn was prepared from human transferrin. First, transferrin was digested twice with Pronase (Boehringer Mannheim) in 0.1M borate buffer (pH 8.0) at 37° C. for 12 hours, and resulting sugar peptides were separated by a gel filtration column (Toyoperl HW-40, 2.6×100 cm, Tosoh, Tokyo) previously equilibrated with 10 mM acetate buffer (pH 6.0).

Next, the separated sugar peptide was digested with enzymes sialidase (from *Arthrobactor ureafacience*, available from Nakalai Tesque, Kyoto, Japan) and β-galactosidase (from jack beam, available from Seikagaku Co., Japan) to obtain GnGn-Asn. GnGn-Ans Sepharose was obtained by reacting 100 μmol GnGn-Asn with 10 ml of activated CH-Sepharose (Pharmacia) to link them.

(2) Phenyl-Sepharose column chromatography 280 ml of Phenyl-Sepharose was filled to a 4.5×18 cm column, and the column was equilibrated with 1.5 L of 20 mM potassium phosphate buffer (pH 6.8, ammonium sulfate 40% saturation). 1.3 L of the concentrated culture supernatant prepared in Example 1 was saturated with ammonium sulfate to 40% saturation, centrifuged at 3000×G for 30 minutes, and the resulting supernatant was absorbed to the column.

Elution was carried out by a linear gradient from ammonium sulfate 40% to 0% in 20 mM potassium phosphate buffer (pH 6.8); at a flow rate of 3 ml/min. Absorption at 280 nm and GnT-V enzyme activity were measured. As shown in FIG. 1, the peak of GnT-V was eluted after the peak of absorption at 280 nm.

(3) Hydroxyapatite column chromatography

Figure 2:
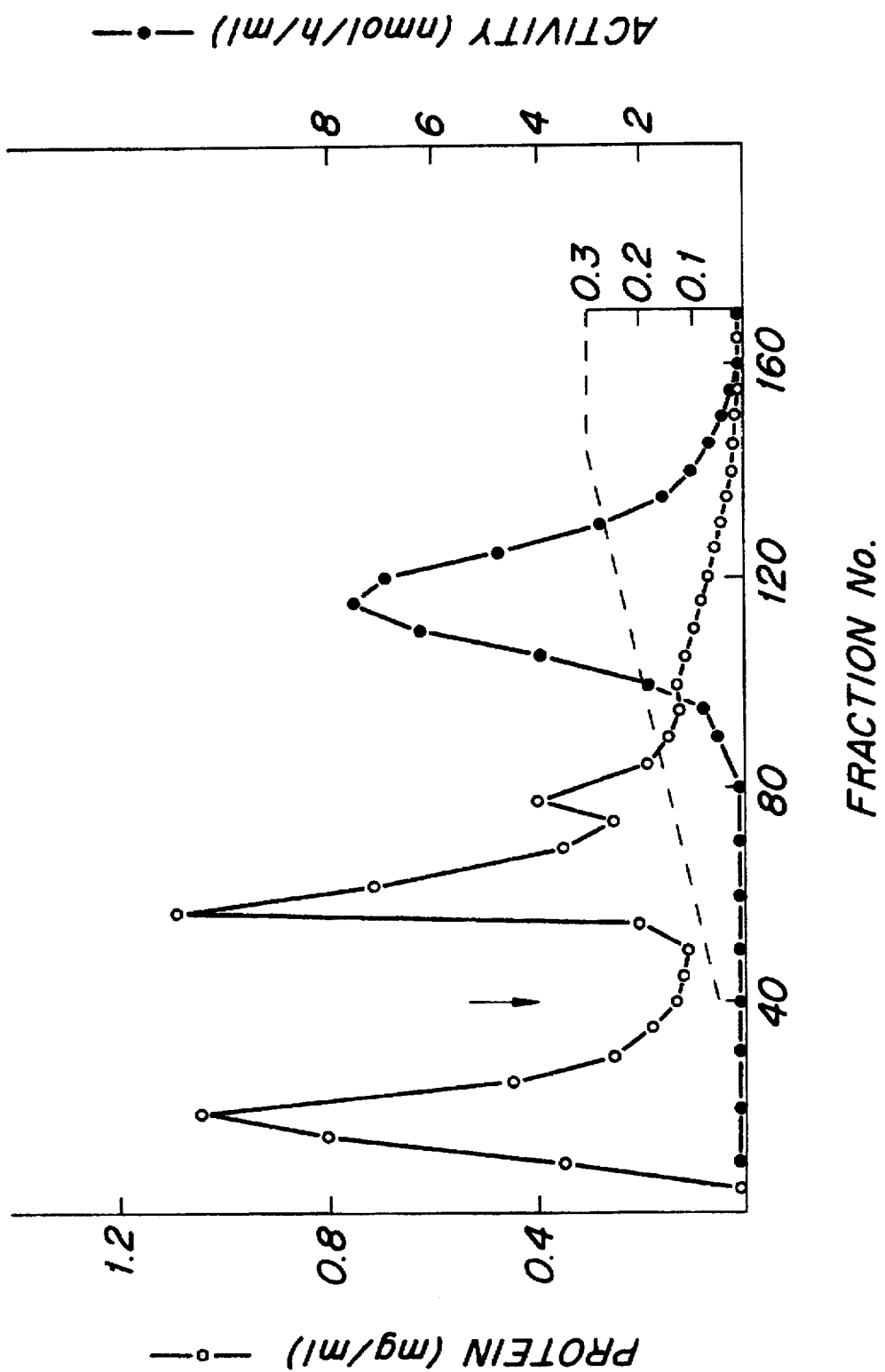
FIG. 2 shows an elution profile of hydroxyapatite column chromatography, wherein open circles linked with solid lines show elution profile of protein, and solid circles linked with solid lines show GnT-V activity. In this figure, the arrow shows the starting point of flow of elution buffer. The elution was carried out by forming a concentration gradient from 50 mM to 300 mM phosphate buffer. Concentration of phosphate buffer is shown by a broken line.

The fractions showing GnT-V enzyme activity eluted from the Phenyl-Sepharose column chromatography were collected, and concentrated with an Amicon YM-30 membrane while simultaneously exchanging the original medium with 20 mM potassium phosphate (pH 6.8). The concentrated fraction was then adsorbed to 55 ml of hydroxyapatite equilibrated with 300 ml of 20 mM potassium phosphate buffer (pH 6.8). Elution was carried out by a linear gradient of 50 mM–300 mM potassium phosphate buffer (pH 6.8) at a flow rate of 3 ml/min. An elution profile of the hydroxyapatite chromatography is shown in FIG. 2. The peak of GnT-V enzyme activity was eluted separately from most of other proteins.

(4) UDP-hexanolamine Agarose-column chromatography

Figure 3:
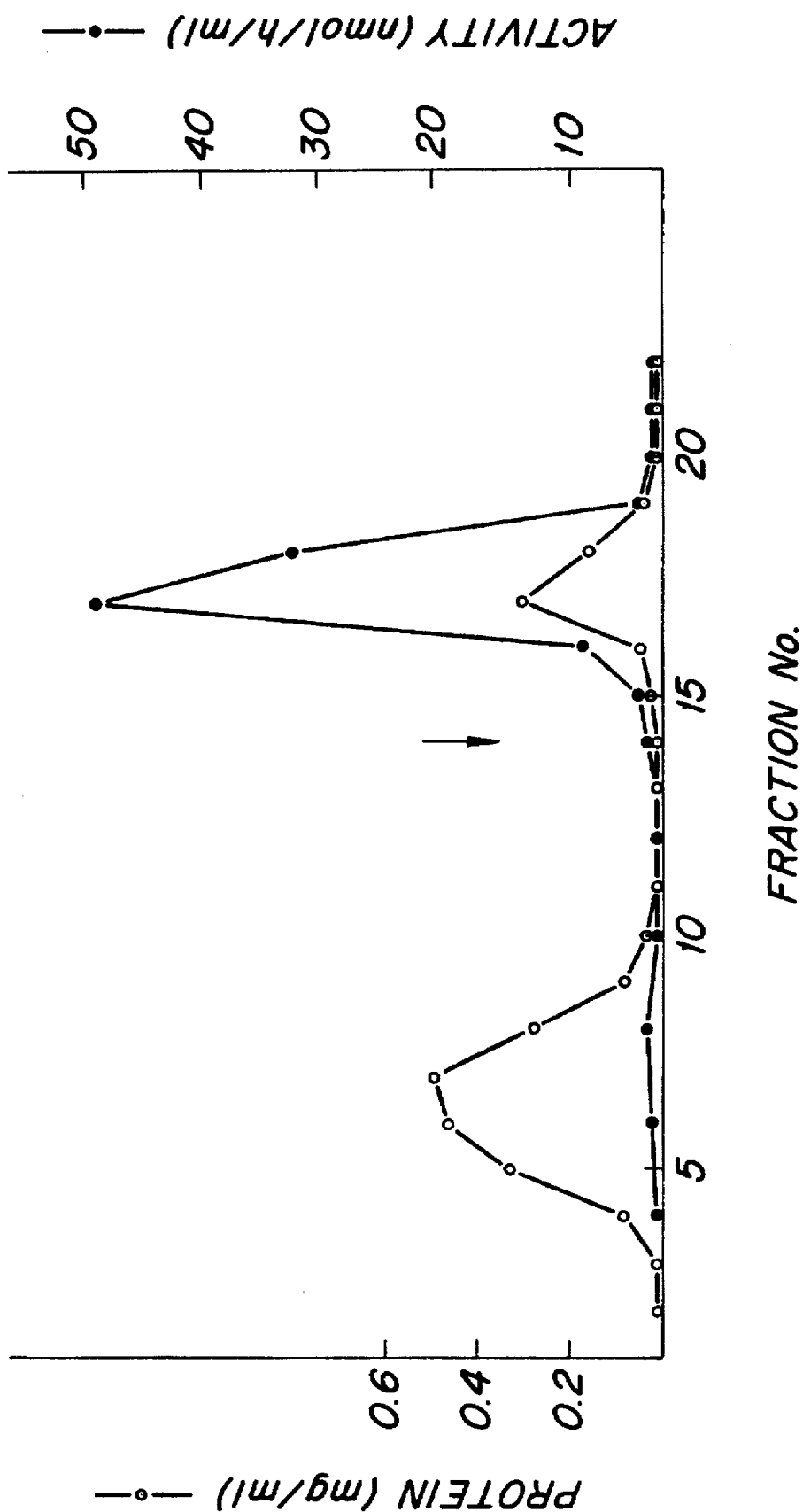
FIG. 3 shows an elution profile of UDP-hexanolamine Agarose-column chromatography, wherein open circles linked with solid lines show an elution profile of protein, and solid circles linked with solid lines show GnT-V activity. In the figure, the arrow shows the start point of flow of elution buffer. The elution was carried out by flowing 0.3M NaCl at a flow rate of 3 ml/hour.

Next, the fractions from the hydroxyapatite column were collected, and the original medium was exchanged with 10 mM potassium phosphate buffer (pH 6.25) using an Amicon YM-30 membrane. The resulting fraction was adsorbed to 20 ml of UDP-hexanolamine Agarose column previously equilibrated with 100 ml of 10 mM potassium sulfate buffer (pH 6.25). Enzyme was eluted with 10 mM potassium phosphate containing 0.3M NaCl, at a flow rate of 15 ml/min. This elution profile is shown in FIG. 3.

(5) GnGn-Asn Sepharose column chromatography

Figure 4:
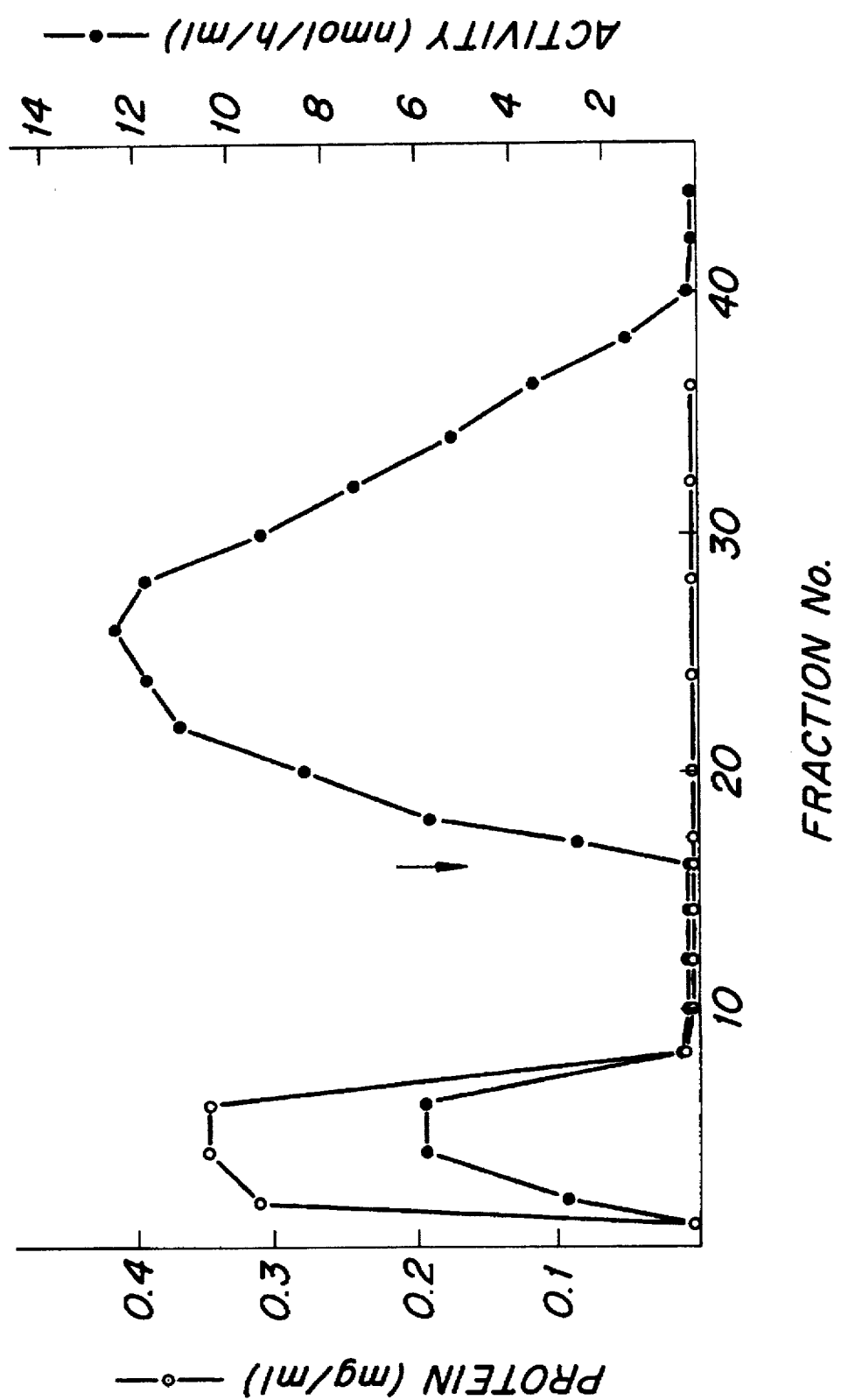
FIG. 4 shows an elution profile of GnGn-Asn Sepharose-column chromatography, wherein open circles linked with solid lines show an elution profile of protein, and solid circles linked with solid lines show GnT-V activity. In the figure, the arrow shows the start point of flow of elution buffer. The elution was carried out by flowing 0.3M NaCl at a flow rate of 3 ml/hour.

Finally, GnGn-Asn Sepharose column chromatography was carried out. The active fraction from the UDP-hexanolamine Agarose column was adsorbed to 4 ml of GnGn-Asn Sepharose equilibrated with 20 ml of 10 mM potassium phosphate buffer (pH 6.25) containing 0.3M NaCl, and after washing the column with same buffer, elution was carried out with 30 mM Tris-HCl (pH 9.0) containing 0.3M NaCl at a flow rate of 3 ml/hour. A result is shown in FIG. 4.

Purification yield of the above-mentioned purification process is shown in Table 1. Each step provided more than 70% yield, and final purification ratio was about 20,000.

TABLE 1

Purification steps from culture supernatant of QG cells derived from human lung carcinoma (small cell cancer), cultured in protein-free medium, and corresponding purification yield

| Steps | Protein (mg) | Specific Acitivity (nmol/h/mg) | Yield % | Purification ratio |
|---|---|---|---|---|
| Medium(*) | 3,250 | 0.4 | 100 | 1 |
| Phenyl-Sepharose | 330 | 2.9 | 71 | 7 |
| Hydroxyapatite | 110 | 8.4 | 67 | 20 |
| UDP-hexanolamine-Agarose | 12.6 | 56.7 | 52 | 135 |
| GnGn-Asn-Sepharose | 0.06 | 8323 | 37 | 19,800 |

(*)1.3L culture supernatant

Example 3

ADS polyacrylamide gel electrophoresis and native polyacrylamide gel electrophoresis SDS polyacrylamide gel electrophoresis was carried out according to reported method (Laemmli, U. K., Nature 227, 680–685, 1970), using 10–15% gradient polyacrylamide gel under the reducing condition and non reducing condition. As molecular weight markers, α-lactalbumin (Mmolecular weight 14,400), soybean trypsin inhibitor (M.W. 20,100), carbonic anhydrase (M.W. 30,000), ovalbumin (M.W. 43,000), bovine serum albumin (M.W. 67,000), and phosphorylase b(M.W. 94,000) were used.

Figure 5:
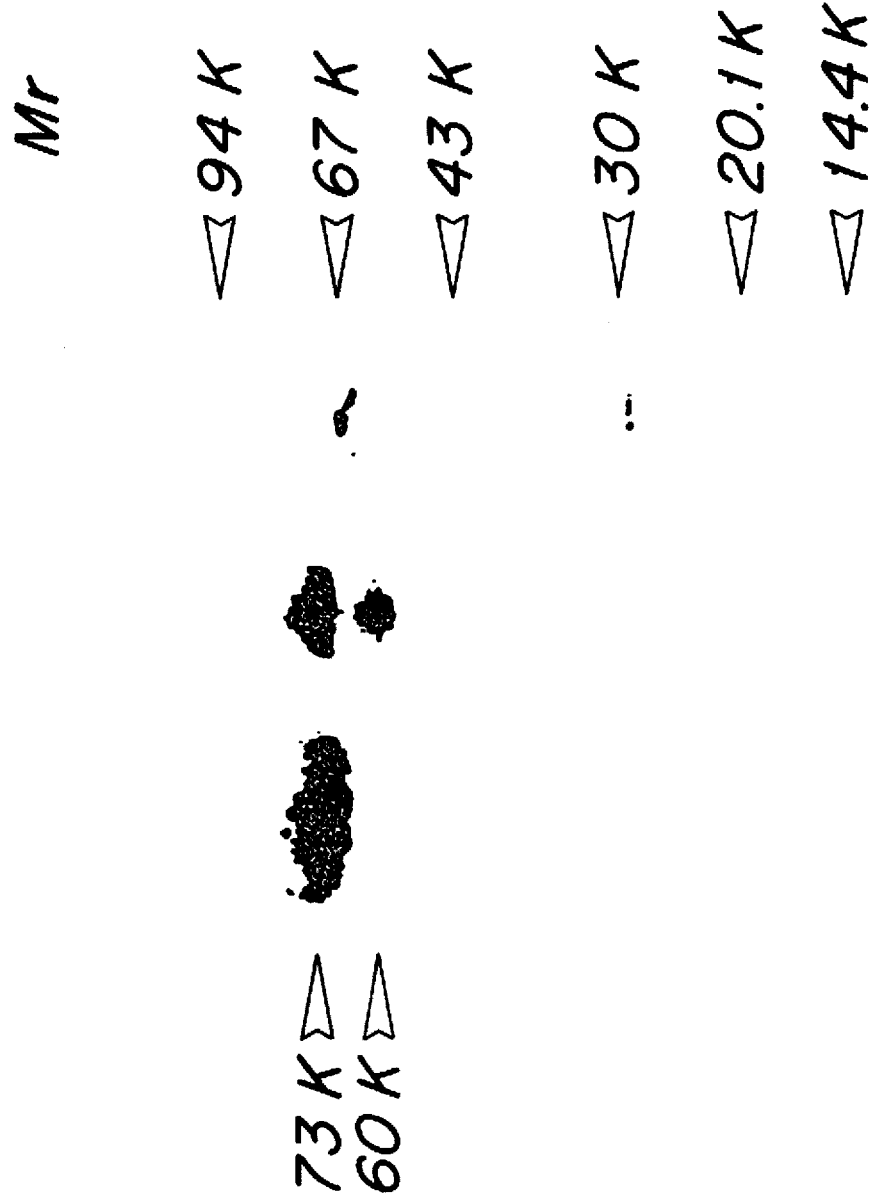
FIG. 5 shows a result of SDS polyacrylamide gel electrophoresis of the present enzyme.
Figure 6:
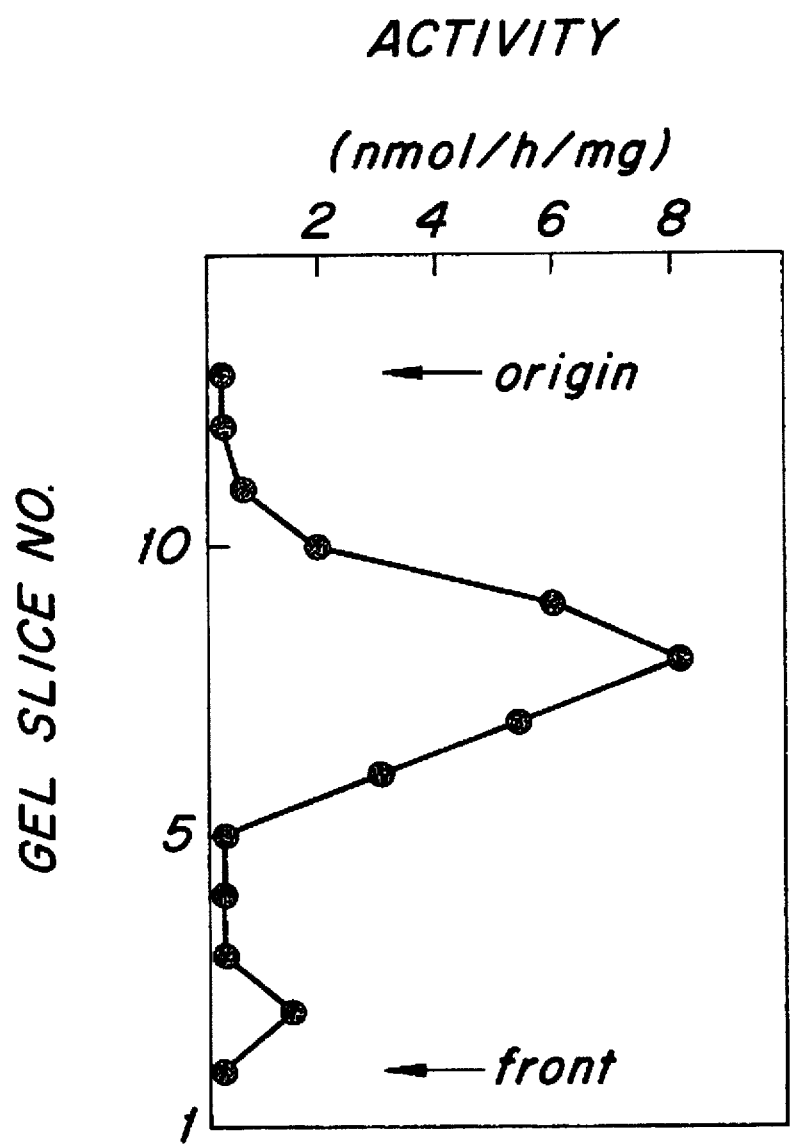
FIG. 6 shows a result of native polyacrylamide gel electrophoresis of the present enzyme.

A photograph of the gel prepared by staining the present enzyme with Coomassie Brilliant Blue is shown in FIG. 5. In an SDS polyacrylamide gel electrophoresis under the non-reducing condition, a single band having a molecular weight of 73 kDa was determined by comparison with the above-mentioned molecular weight markers was observed. On the other hand in an SDS polyacrylamide gel electrophoresis under the reducing condition, a band of 60 kDa in addition to the band of 73 kDa were observed on the gel. A photograph of a gel of native polyacrylamide gel electrophoresis stained with Coomassie Brilliant Blue and enzyme activity of sections excised from the native polyacrylamide gel electrophoresis are shown in FIG. 6. Levels of the enzyme activity were observed dependent on the densities of the bands. From the above, it was confirmed that the isolated and purified protein is a desired GnT-V.

Example 4

Peptide mapping analysis

SDS polyacrylamide gel electrophoresis was carried out under a reducing condition, and bands corresponding to 60 kDa and 73 kDa were excised from the gel. To the sliced gel pieces was added 30 mM Tris-HCl (pH 6.5) containing 0.5% SDS, which was then boiled, and protein was extracted with an elctroelution apparatus. After the elution, the protein was digested with 200 ng of trypsin (Sigma, St. Louis, Mo.), dissolved in 50 mM Tris-HCl (pH 8.0) at 37° C. for 11 hours.

Figure 7:
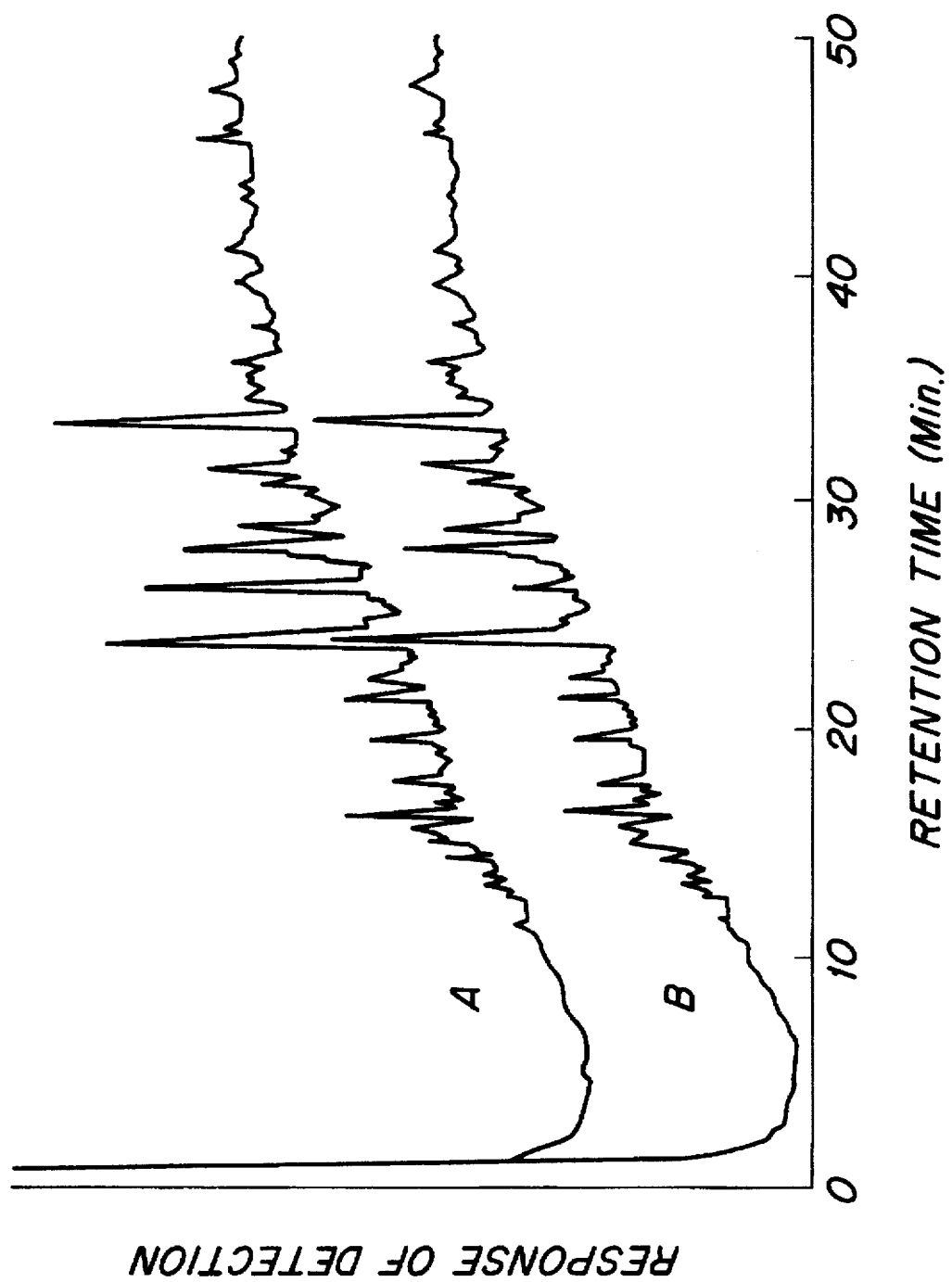
FIG. 7 shows a peptide mapping analysis of the present enzyme.

The digestion product was applied to a reverse phase high performance liquid chromatography (Chemcosorb 3 ODS-H, Osaka Japan, 2.1×75 mm), and eluted under an acidic condition (0.1% TFA) using 0–60% acetonitrile gradient. An elution profile is shown in FIG. 7. The proteins of 60 kDa and 73 kDa show similar elution profiles and therefore it is concluded that both of the proteins comprise basically the same polypeptide, though there is possibility that they are partially enzymatically digested.

Example 5

Determination of partial amino acid sequences

To determine the amino acid sequences, the peptide fragments obtained in Example 2 from purified GnT-V were subjected to a Gas-phase sequencer (Applied Biosystem Inc. Foster City, Calif.), and the following sequences were obtained.

(SEQ ID NO:1) Thr-Pro-Trp-Gly-Lys (SEQ ID NO:2) Asn-Ile-Pro-Ser-Tyr-Val (SEQ ID NO:3) Val-Leu-Asp-Ser-Phe-Gly-Thr-Glu-Pro-Glu-Phe-Asn-His-Ala-Asn-Tyr-Ala (SEQ ID NO:4) Asp-Leu-Gln-Phe-Leu-Leu (SEQ ID NO:5) Asn-Thr-Asp-Phe-Phe-Ile-Gly

Example 6

Substrate Specificity

Substrate specificity was determined using the following compound as sugar acceptors according to the above-mentioned enzyme activity measuring method.

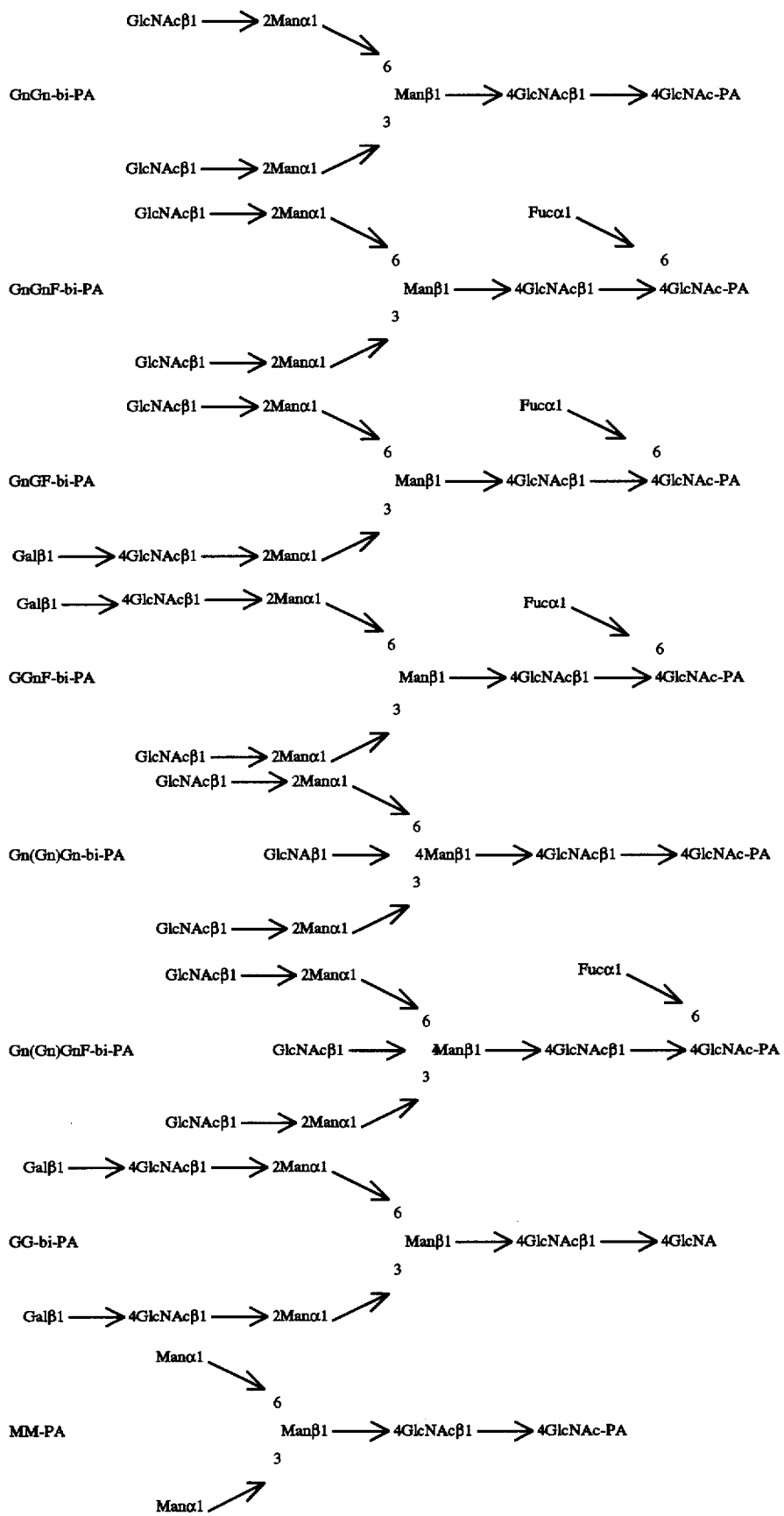

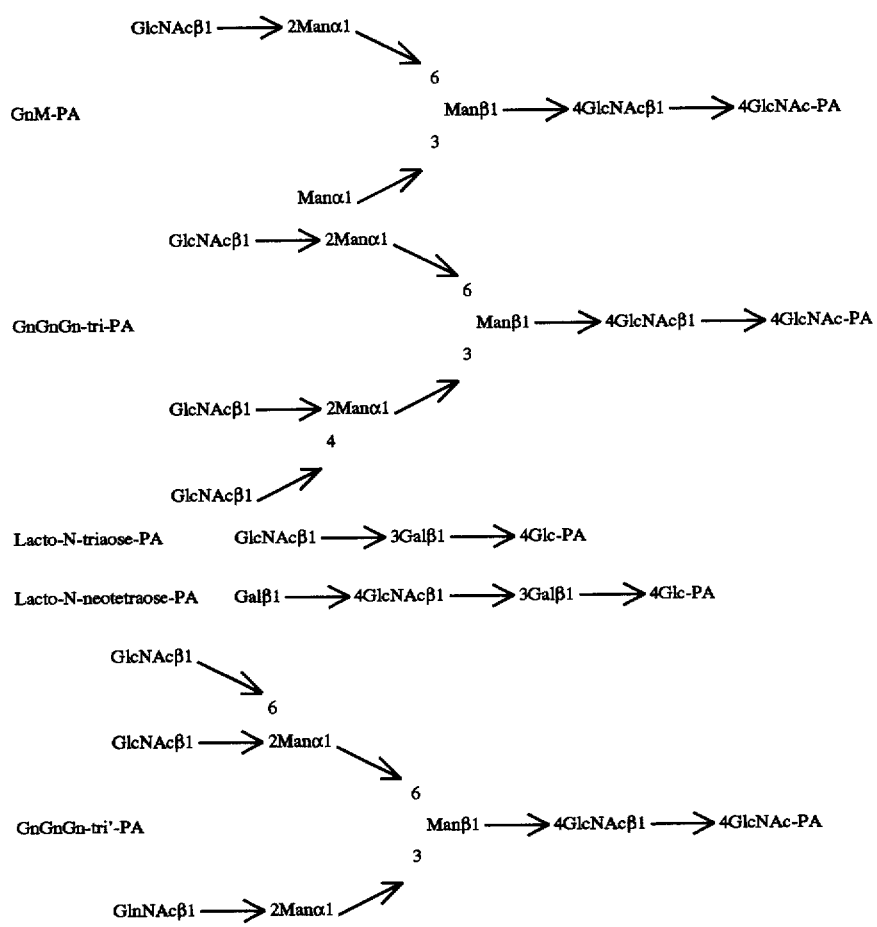

GnGnGn-tri'-PA (GlcNAcβ1-2Manα1-3 (GlcNAcβ1-2 (GlcNAcβ1-6)Manα1-6) -Manβ1-4GlcNacβ1-4GlcNAc-2-aminopyridine)

GnGnF-, GnGF-, GGnF-, Gn(Gn)GnF-, Gn(Gn)Gn-, GG-, GnGn-, MM- and GnM- were isolated from the bovine IgG treated with anhydrous hydrazine and then labeled with a fluorescence label according to Hase et al. method (Hase, S., Ibuki, T., and Ikehara, T., J. Biochem. 95, 197–203 (1984). The purified GnT-V was diluted with PBS buffer to a final concentration of 0.1 mg protein/ml, and then reacted with each fluorescence-labeled sugar acceptor. A result is shown in Table 2.

TABLE 2

Substrate Specificity of the Present Enzyme to Various Sugar Acceptors

| Acceptor (70 μM) | Relative reaction rate |
|---|---|
| GnGn-bi-PA (GlcNAcβ1-2Manα1-3-(GlcNAcβ1-2Manα1-6)Manβ1-4GlcNAcβ1-4GlcNAc-2-aminopyridine) | 100 |
| GnGnF-bi-PA (GlcNAcβ1-2Manα1-3-(GlcNAcβ1-2Manα1-6)Manβ1-4GlcNAcβ1-4GlcNAc(Fucα1-6)-2-aminopyridine) | 78 |
| GnGF-bi-PA (Galβ1-4GlcNACβ1-2Manα1-3(GlcNAcβ1-2Manα1-6)Manβ1-4GlcNAcβ1-4GlcNAc(Fucα1-6)-2-aminopyridine) | 3 |
| GGnF-bi-PA GlcNAcβ1-2Manα1-3(Galβ1-4GlcNAc B1-2Manα1-6)Manβ1-4GlcNAcβ1-4GlcNAc(Fucβ1-6)-2-aminopyridine) | 0.2 |
| Gn(Gn)Gn-bi-PA (GlcNAcβ1-2Manα1-2Manα1-6)-Manβ1-4GlcNAcβ1-4GlcNAc-2-aminopyridine) | 0 |
| Gn(Gn)GnF-bi-PA (GlcNAcβ1-2Manα1-2Manα1-6)-Manβ1-4GlcNAcβ1-4GlcNAc(Fucα1-6)2-aminopyridine) | 0 |
| GG-bi-PA (Galβ1-4GlcNAcβ1-2Manα1-3(Galβ1-4GlcNAcβ1-2Manα1-6)Manβ1-4GlcNAcβ1-4GlcNAc-2-aminopyridine) | 0 |
| MM-PA (Manα1-3Manα1-6)Manβ1-4GlcNAcβ1-4GlcNA-2-aminopyridine | 0 |
| GnM-PA (Manβ1-3(GlcNAcβ1-2Manα1-6)Manβ1-4 GlcNAcβ1-4GlcNAc-2-aminopyridine) | 66 |
| GnGnGn-tri-PA (GlcNAcβ1-2(GlcNAcβ1-4)Manα1-3(GlcNAcβ1-2Manα1-6)-Manβ1-4GlcNAcβ1-4GlcNAc-2-aminopyridine) | 125 |

TABLE 2-continued

Substrate Specificity of the Present Enzyme to Various Sugar Acceptors

| Acceptor (70 μM) | Relative reaction rate |
|---|---|
| Lacto-N-triaose-PA (GlcNAcβ1-3Galβ1-4Glc-2-aminopyridine) | 0 |
| Lacto-N-neotetraose-PA (Galβ1-4GlcNAcβ1-3Galβ1-4Glc-2-aminopyridine) | 0 |

Gn, N-acetyl-D-glucosamine;
G (Gal), galactose;
PA, 2-aminopyridine;
M, (Man), D-Mannose;
F, (Fuc), fucose;
GlcNAc, N-acetylglucosamine It was found that the present enzyme reacts with all of GnGnF-bi-PA, GnM-PA and GnGnGn-tri-PA.

Example 7

Optimum pH

Figure 8:
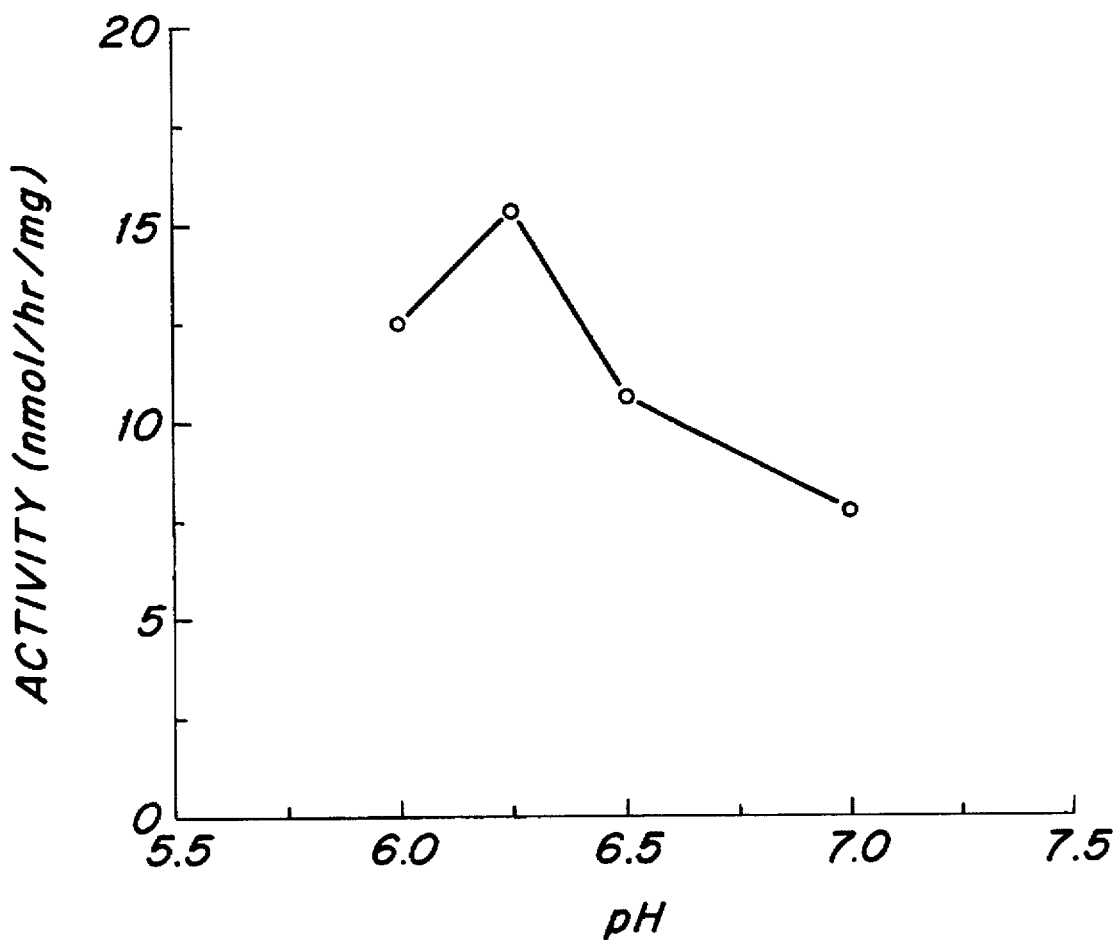
FIG. 8 is a graph showing optimum pH of the present enzyme.

Assay mixtures containing 0.2M GlcNAc, 40 mM EDTA, 1% Triton X-100, and 40 mM UDP-GlcNAc in 0.25M potassium phosphate buffer of pH 6.0, 6.25, 6.5 or 7.0 was obtained. To 25 μl of the assay mixture were added 15 μl of a test sample and 10 μl of a substrate (GnGn-bi-PA), and the mixture was incubated at 37° C. for 4 hours. A result is shown in FIG. 8.

Example 8

Isolation and identification of cDNA for GnT-V and Construction of expression vector Oligomer S18 shown in SEQ ID No: 6 was synthesized on the basis of the amino acid sequence shown in SEQ ID No: 3 obtained in Example 5, and oligomer A21 shown in SEQ ID No: 7 was synthesized on the basis of the amino acid sequence shown in SEQ ID No: 5.

Double-stranded cDNA was synthesized from RNA having poly A prepared from QG cells using a cDNA synthesis kit (Pharmacia). Next, PCR was carried out using said cDNA as a templete, and the oligomers S18 and A21 as primers, and using Ampli-Taq DNA polymerase (Takara). As a result, a DNA fragment of about 500 base pairs (bp) which is a fragment of GnT-V cDNA was obtained.

Next, further cDNA cloning was carried out using the cDNA thus obtained as a probe. Namely, this cDNA was used as a templete and labeled with α32P-CTP using a random primer labeling kit (Amersham). The probe thus obtained was used to screen a human fetal liver cDNA library (Clontech Laboratories Inc.) according to a conventional procedure. Among the clones thus obtained, the longest clone was excised with EcoRI, and subcloned into pBluescript II ks(+) (Strate gene). Since the insert contains an EcoRI site, two fragments were obtained. Each of the two fragments was sequences, and B fragment of about 800 bp, and F fragment of about 1200 bp were obtained.

The sequences of the DNA fragments thus obtained were determined by Sequenase (U SB), and a result shown in SEQ ID NO: 8 was obtained. It was confirmed that this DNA fragment contains all the nucleotide sequences encoding five amino acid sequences obtained in Example 5.

Note, the cDNA fragment for GnT-V thus obtained does not reach to the stop codon at the 3'-terminus, and therefore a 3'-terminal nucleotide sequence has not yet been determined, but it is easy to determine the 3'-terminal nucleotide sequence for a person with ordinary skill in the art.

Figure 9:
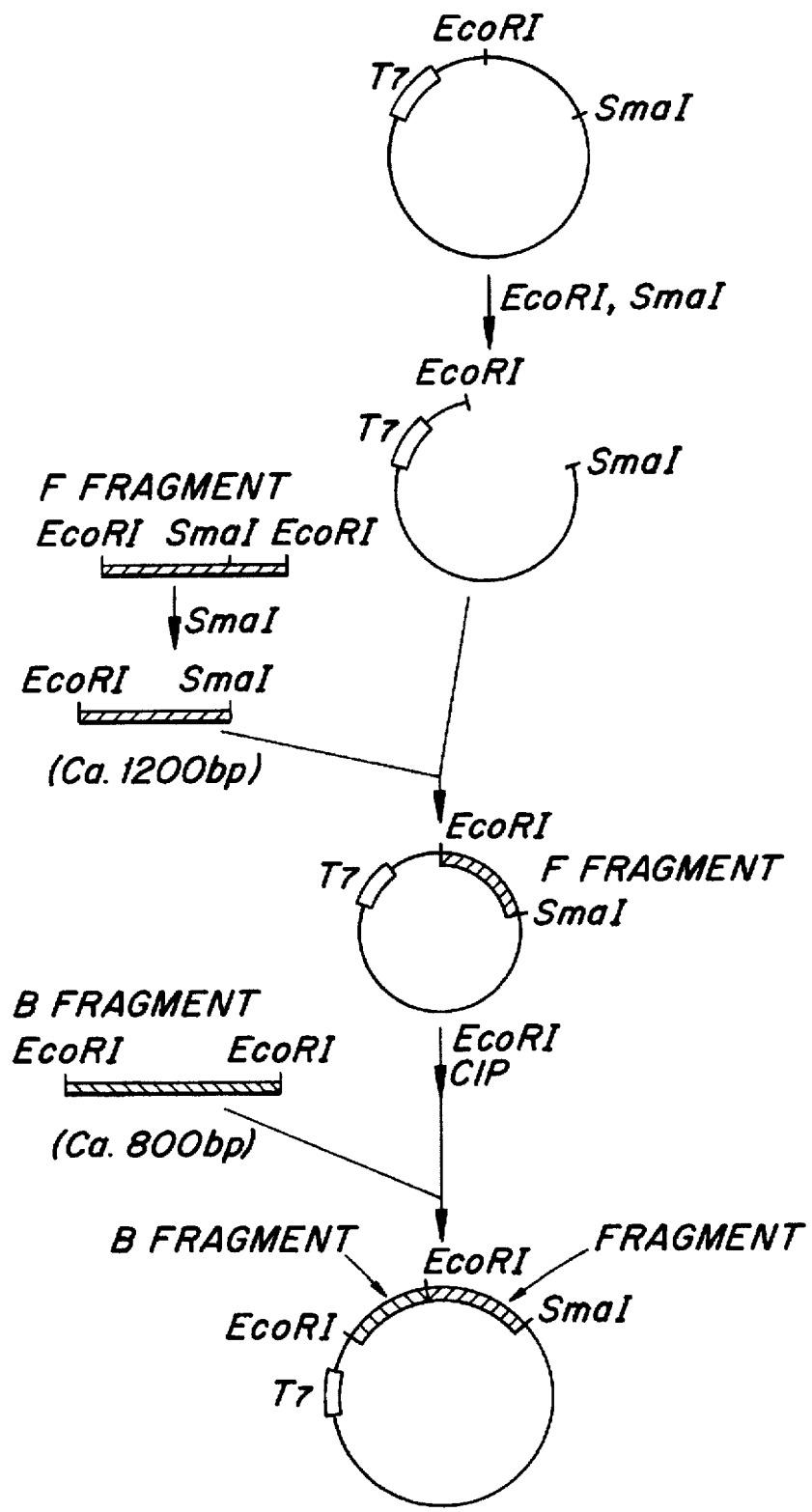
FIG. 9 represents a construction process of the present expression vector.

Next, to express the GnT-V cDNA fragment in animal cells, the cDNA fragment was inserted into an expression vector. Namely, an expression vector pSVK3 (Pharmacia) was digested with EcoRI and SmaI so that the above-mentioned F fragment was excised at the EcoRI site and the SmaI site inside of the insert, and inserted into an expression vector (see, FIG. 9).

Next, the vector incorporating the F fragment was cleaved with EcoRI, and treated with CIP (calf intestinal phosphatase) to prevent self-ligation. Next, the B fragment excised at EcoRI sites was inserted into the above-treated expression vector to construct an expression vector containing both the F fragment and B fragment.

Example 9

Expression of cloned GnT-V cDNA and enzyme activity of the expressed protein The expression vector constructed in Example 8 was used to express the GnT-V cDNA fragment in animal cells and GnT-V activity of the expressed protein was tested.

Figure 10:
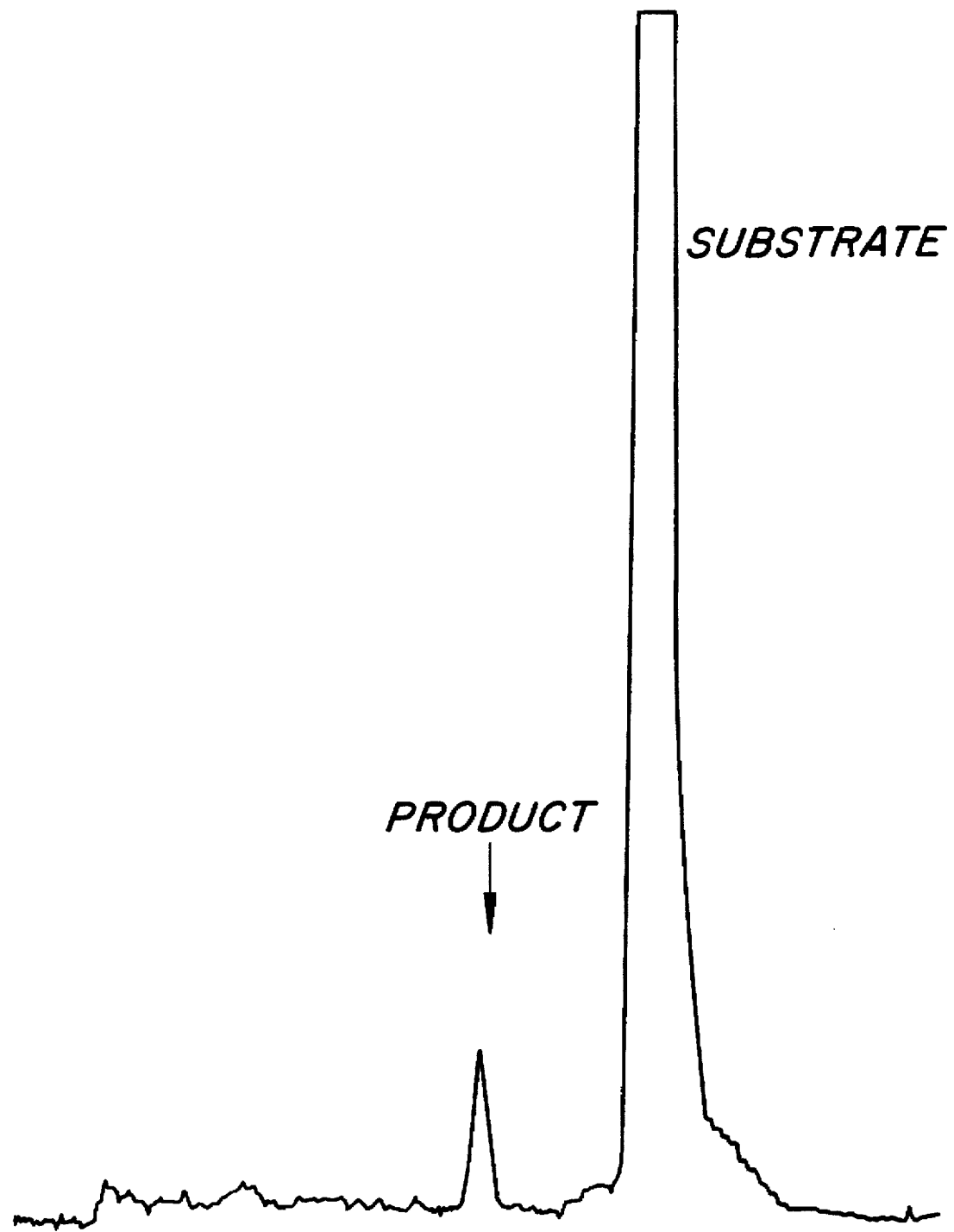
FIG. 10 is an elution profile of a high performance liquid chromatography showing that the present expression product, GnT-V, converts a substrate GnGn-bi-PA to a product GnGnGn-tri'-PA.

Expression vector containing GnT-V cDNA fragment was transfected to COS-1 cells, animal cells for expression, by electroporation. Namely, about $5 \times 10^6$ CO.S-1 cells previously prepared were suspended in HEPES buffer (50 mM Hepes, 137 mM NaCl, 5 mM KCl, 0.7 mM NaHPO$_3$, 6 mM dextrose, pH 7.05), 60 μg of the above-mentioned plasmid was added thereon, and 800 μl of the suspension was subjected to electroporation in an electroporator (Bio-Rad) at 250 V, 960 mF. Next, all the suspensions of COS-1 cells electroporated with GnT-V gene was plated in a petri dish having the diameter of 6 cm, and cultured at 37° C. in 5% $CO_2$ for 48 hours. The cultured cells were collected with a rubber-coated police man bar, and suspended in 50 μl of PBS buffer, and the cells were disrupted with a sonicator. Next, the disruptant was centrifuged to collect a supernatant, and 15 μl of the supernatant was used to assay enzyme activity. A result is shown in FIG. 10.

From the result, it was confirmed that the cloned GnT-V cDNA fragment contain a minimum length necessary for expression of desired enzyme activity.

According to the present invention, UDP-N-acetylglucosamine: α-6-D-mannoside, β1,6-N-acetylglucosaminyl transferase was isolated and purified from a culture supernatant of QG cells derived from human lung cancer cells, cultured in a protein-free medium, and properties and partial amino acid structure thereof were determined. Moreover, the present inventors clarified substrate specificity to various sugar acceptors, using the purified enzyme. The sugar transfer enzyme having such specificity is an important enzyme responsible for control of sugar chain biosynthesis path way. Moreover, it is now being clarified that the present enzyme participates to modification of sugar chains accompanying malignant alteration of cells.

Considering the above, not only is the present enzyme useful as a marker for malignancy of cells, but also by establishing a screening system for specific inhibitors against the present enzyme, it becomes possible to design cancer-metastasis inhibitors. In addition, since β(1,6) branch structure can be introduced into various sugar acceptors exemplified using the present invention, oligosaccharides having β(1,6) branch structure can be industrially produced. Moreover, from an aspect of sugar chain technology, homogeneous formation of sugar chains in the production of desired substance by genetic engineering is possible by using a large amount of the present enzyme.

We claim:

1. An isolated β1,6-N-acetylglucosaminyl transferase having the following properties:

(1) Action: it transfers N-acetylglucosaminyl from uridine-5'-diphospho-N-acetylglucosamine to α-6-D-mannoside;

(2) Substrate specificity: it shows a reactivity of about 79% for GnGnF-bi-PA (GlcNAcβ1-2Manα1-3-(GlcNAcβ1-2Manα1-6)Manβ1-4GlcNAcβ1-4GlcNAc (Fucα1-6)-2-aminopyridine), about 125% for GnGnGn-tri-PA (GlcNAcβ1-2) (GlcNAcβ1-4)Manα1-3(GlcNAcβ1-2Manα1-6)-Manβ1-4GlcNAcβ1-4GlcNAc-2-aminopyridine) and about 66% for GnM-PA (Manα1-3(GlcNAcβ1-2Manα1-6)Manβ1-4GlcNAcβ1-4GlcNAc-2-aminopyridine), with the reactivity for GnGn-bi-PA (GlcNAcβ1-2Manα1-3-(GlcNAcβ1-2Manα1-6)Manβ1-4GlcNAcβ1-4GlcNAc-2-aminopyridine) being defined as 100%;

(3) Optimum pH: 6.2 to 6.3;

(4) Inhibition, Activation and Stability: $Mn^{2+}$ is not necessary for expression of activity, and the activity is not inhibited in the presence of 20 mM EDTA;

(5) Molecular weight: about 73,000 as determined by SDS-PAGE in the absence of reducing agent; and about 73,000 and about 60,000 as determined in the presence of a reducing agent;

(6) Km value: 133 μM and 3.5 mM for acceptor GnGn-bi-PA (GlcNAcβ1-2Manα1-3-(GlcNAcβ1-2Manα1-6)Manβ1-4GlcNAβ1-4GlcNAc-2-aminopyridine) and donor UDP-GlcNAc (uridine-5'-diphospho-acetylglucosamine), respectively; and (7) It includes the following peptide fragments:

| | |
   |---|---|
   | (SEQ ID NO. 1) | Thr—Pro—Trp—Gly—Lys |
   | (SEQ ID NO. 2) | Asn—Ile—Pro—Ser—Tyr—Val |
   | (SEQ ID NO. 3) | Val—Leu—Asp—Ser—Phe—Gly—Thr—Glu—Pro Glu—Phe—Asn—His—Ala—Asn—Tyr—Ala |
   | (SEQ ID NO. 4) | Asp—Leu—Gln—Phe—Leu—Leu |
   | (SEQ ID NO. 5) | Asn—Thr—Asp—Phe—Phe—Ile—Gly. |

2. An isolated β1,6-N-acetylglucosaminyl transferase encoded by the nucleotide sequence of SEQ ID No: 8.

3. An isolated β1,6-N-acetylglucosaminyl transferase having a nucleotide sequence having one or more nucleotide modifications in the nucleotide sequence of SEQ ID No: 8.

4. The isolated β1,6-N-acetylglucosaminyl transferase according to claim 3 wherein the modification is an addition, deletion, replacement with other nucleotides, or a combination thereof.

5. The β1,6-N-acetylglucosaminyl transferase of claim 1, wherein the transferase is of human origin.

6. The β1,6-N-acetylglucosaminyl transferase of claim 1, wherein the transferase is derived from lung carcinoma cells.

7. The β1,6-N-acetylglucosaminyl transferase of claim 5, wherein the transferase is derived from human lung carcinoma cells.

8. The β1,6-N-acetylglucosaminyl transferase of claim 7, wherein the transferase is derived from human lung carcinoma SBM331 (FERM BP-3967).

9. The β1,6-N-acetylglucosaminyl transferase of claim 1, wherein the transferase is purified from a protein-free culture.

10. The β1,6-N-acetylglucosaminyl transferase of claim 1, wherein the transferase is extracellularly secreted.

* * * * *